US006608628B1

(12) United States Patent
Ross et al.

(10) Patent No.: US 6,608,628 B1
(45) Date of Patent: Aug. 19, 2003

(54) METHOD AND APPARATUS FOR VIRTUAL INTERACTIVE MEDICAL IMAGING BY MULTIPLE REMOTELY-LOCATED USERS

(75) Inventors: Muriel D. Ross, Albuquerque, NM (US); Ian Alexander Twombly, Santa Clara, CA (US); Steven O. Senger, Onalaska, WI (US)

(73) Assignee: The United States of America as represented by the Administrator of the National Aeronautics and Space Administration (NASA), Washington, DC (US)

(*) Notice: Subject to any disclaimer, the term of this patent is extended or adjusted under 35 U.S.C. 154(b) by 0 days.

(21) Appl. No.: 09/436,716

(22) Filed: Nov. 5, 1999

Related U.S. Application Data

(60) Provisional application No. 60/107,286, filed on Nov. 6, 1998, provisional application No. 60/107,509, filed on Nov. 6, 1998, provisional application No. 60/107,284, filed on Nov. 6, 1998, and provisional application No. 60/107,390, filed on Nov. 6, 1998.

(51) Int. Cl.[7] ............................ G06F 9/00; G06F 15/16; G06F 15/173; G09G 5/00
(52) U.S. Cl. ................. 345/619; 345/723; 345/733; 345/734; 345/751; 345/756; 709/107; 709/204; 709/231; 382/128; 382/154
(58) Field of Search ................. 345/733, 734, 345/735, 736, 737, 740, 741, 744, 748, 750, 751, 753, 761, 619, 700, 719, 723, 732, 756; 709/223, 219, 315, 107, 201, 204, 205, 100, 200, 231, 232, 246; 703/1, 104.1

(56) References Cited

U.S. PATENT DOCUMENTS 5,515,491 A * 5/1996 Bates et al. ................. 345/155

5,740,176 A * 4/1998 Gupta et al. ................. 370/440

(List continued on next page.)

FOREIGN PATENT DOCUMENTS

EP 1058191 * 12/2000 ........... G06F/11/14

OTHER PUBLICATIONS

"World Tool Kit Reference Manual," Release 8, Sense8 Corporation, 1991–1998, Chapter 1,4,7 and 22.
Ross, et al., "New Approaches To Virtual Environment Surgery," Medicine Meets Virtual Reality. J.D. Westwood, et al. (Eds), IOS Press 1999, pp. 297–301.

(List continued on next page.)

Primary Examiner—Matthew C. Bella
Assistant Examiner—Wesner Sajous
(74) Attorney, Agent, or Firm—Robert M. Padilla; Carla M. Wong

(57) ABSTRACT

A virtual interactive imaging system allows the displaying of high-resolution, three-dimensional images of medical data to a user and allows the user to manipulate the images, including rotation of images in any of various axes. The system includes a mesh component that generates a mesh to represent a surface of an anatomical object, based on a set of data of the object, such as from a CT or MRI scan or the like. The mesh is generated so as to avoid tears, or holes, in the mesh, providing very high-quality representations of topographical features of the object, particularly at high-resolution. The system further includes a virtual surgical cutting tool that enables the user to simulate the removal of a piece or layer of a displayed object, such as a piece of skin or bone, view the interior of the object, manipulate the removed piece, and reattach the removed piece if desired. The system further includes a virtual collaborative clinic component, which allows the users of multiple, remotely-located computer systems to collaboratively and simultaneously view and manipulate the high-resolution, three-dimensional images of the object in real-time.

20 Claims, 26 Drawing Sheets

U.S. PATENT DOCUMENTS

| | | | | | |
|---|---|---|---|---|---|
| 5,742,778 | A | * | 4/1998 | Hao | 395/332 |
| 6,011,537 | A | * | 1/2000 | Slotznick | 345/619 |
| 6,148,066 | A | * | 11/2000 | Di Santo | 379/93.19 |
| 6,182,123 | B1 | * | 1/2001 | Filepp | 709/217 |
| 6,192,320 | B1 | * | 2/2001 | Margrey | 702/34 |
| 6,215,785 | B1 | * | 4/2001 | Batruci | 370/360 |
| 6,295,513 | B1 | * | 9/2001 | Thackston | 703/1 |
| 6,356,758 | B1 | * | 3/2002 | Almeida et al. | 455/446 |
| 6,411,965 | B2 | * | 6/2002 | Klug | 707/201 |
| 6,525,732 | B1 | * | 2/2003 | Gadh et al. | 345/428 |

OTHER PUBLICATIONS

Montgomery, et al., "A Method for Semiautomated serial section reconstruction and visualization of Neural Tissue from TEM Images", Biomedical Image Processing and Biomedical Visualization, SPIE–The International Society for Optical Engineering, Feb. 1993, vol. 1905, pp. 114–120.

Montgomery et al., "Improvements In Semiautomated Serial–Section Reconstruction and Visualization of Neural Tissue From TEM Images," SPIE Electronic Imaging, 3D Microscopy Conf Proc., 1994, pp. 264–267.

Montgomery et al., "Non–Fiducial, Shape–Based Registration of Biological Tissue," SPIE vol. 2655, Aug. 1996, pp. 224–232.

Ross, et al., "A National Center for Biocomputation: In Search of a Patient–Specific Interactive Virtual Surgery Workbench," Medicine Meets Virtual Reality, IOS Press and Ohmsha, 1998, pp. 5323–328.

Heather Harreld, "NASA Aids In Virtual Surgery," Federal Computer Week, Nov. 2, 1998.

Andrew Wilson, "Researchers Use Visualization Tools to Render 3–D Medical Images," Vision Systems Design, Dec. 1997, pp. 30–34, 36 and 38.

Bill Curtis, "The Virtual Reality of Medicine," California Computer News, vol. XIV, Dec. 1997, pp. 38–39.

Tamara Grippi, "Robots In Surgery, SVMH Prepares for the Future," The Carmel Pine Cone, Aug. 29, 1997, pp. 10A, 14A, and 15A.

Charles F. King, "Medical Volume Visualization—The Doorway to the Future," Innovation 3, Summer 1997, pp. 40–42, 44–45.

Judy Richter, "A Cut Above Routine Surgery," The San Francisco Examiner, Apr. 6, 1997, pp. B–5–B6.

"From Tang to Robotic Surgery," Space Life Sciences Consortium Newsletter, Division of Space Life Sciences, vol. 5, No. 1, Spring 1997, pp. 1–3.

David Eggleston, "NASA Uses First Immersive Workbench for Surgery Training," Silicon Graphics World, vol. 7, No. 1 Jan. 1997.

Ferrara–Kurth, Kierith, "Researcher Creates Visualization for 3–D Bronchial Fly–Throughs", Silicon Graphics World, vol. 7, No. 1 Jan. 1997.

"Working In Virtual Worlds," Computer Graphics World, Jan. 1997.

Mike Goodkind, "Not Exactly Rocket Science," Stanford Today, Sep./Oct. 1996, pp. 31–32.

Muriel D. Ross, "Biological Neural Networks: Models For Future 'Thinking' Machines," NASA Tech Briefs, vol. 15, No. 6, Jun. 1991, pp. 10, 11 and 131.

Orla Smith, "Visible Human Project Gets Greater Exposure," Nature Medicine, vol. 2, No. 11, Nov. 1996.

"NASA Technology Assists Reconstructive Surgery," Space Technology Innovation, Sep./Oct. 1996, p. 17.

Keller et al., "Visual Cues, Practical Data Visualization," IEEE Computer Society Press, p. 155.

Thomas P. Pearsall, "Close Encounters of the Virtual Kind," Circuits and Devices, Jan. 1999, pp. 10–12.

Susan Okie, "Out of Body Medicine: Doctors Turn to Computer Simulators to Enhance Their Skills," The Washington Post, Nov. 5, 1996, p. Z12.

Grimson, et al., "Image Guided Surgery," Scientific American, Jun. 1999, pp. 63–69.

"How's That For Forward Thinking?" The Spotlight, New Media News, May 2, 1997.

"Virtual Rehearsals For Plastic Surgery," Biophotonics International, Sep./Oct. 1996, p. 33.

"Real Patients, Virtual Surgery," A Fantastic Voyage Through the Human Body, Feb. 1997.

"Surgical Simulator," Popular Mechanics, Feb. 1998, p. 26.

"Software Scalpel For Virtual Surgery," Real Time Graphics, vol. 7, No. 4, Oct./Nov. 1998.

Jane Hutchison, "Biocomputation Center Opens," Astrogram, vol. XXXIII, No. 23, Aug. 16, 1991, p. 1–2.

Scientific Computing & Automation, Jul. 1999, p. 55.

Greg Freiherr, "The Future Arrives for Medical Displays," Medical Device and Diagnostic Industry, Jan. 1997, pp. 92–97.

* cited by examiner

METHOD AND APPARATUS FOR VIRTUAL INTERACTIVE MEDICAL IMAGING BY MULTIPLE REMOTELY-LOCATED USERS

This application claims the benefit of Provisional U.S. Patent Applications No. 60/107,286, filed on Nov. 6, 1998 and entitled "Reconstruction of Serial Sections (ROSS 3-D Reconstruction Program)"; Ser. No. 60/107,509, filed on Nov. 6, 1998 and entitled "Polygon Reduction in 3-Dimensional Meshes"; Ser. No. 60/107,284, filed on Nov. 6, 1998 and entitled "Mesher: Three-Dimensional Surface Generation from Volumetric Data Sets"; and Ser. No. 60/107,390, filed on Nov. 6, 1998 and entitled "Virtual Surgery Cutting Tool", each of which is incorporated herein by reference in its entirety.

ORIGIN OF THE INVENTION

The invention described herein was made in the performance of work under a NASA contract no. NCC2-1006 and is subject to Public Law 96-517 (35 U.S.C. 200 et seq.). The contractor has not elected to retain title to the invention.

FIELD OF THE INVENTION

The present invention pertains to the field of medical imaging systems and techniques. More particularly, the present invention relates to techniques for displaying and manipulating high-resolution, three-dimensional medical images.

BACKGROUND OF THE INVENTION

Various techniques have been developed for imaging internal structures and functions of the human body. Examples of such techniques include computed tomography (CT), magnetic resonance imaging (MRI), echocardigraphy, sonography, and nuclear medicine. The images are commonly generated by first acquiring three-dimensional (3D) data using a tomographic imaging system, and then "reconstructing" the images based on the data. The reconstruction process is normally performed by software executing on a computer system such as a workstation or a personal computer (PC). Advances in computer technology, including increases in the amounts of available processing power, have enabled more sophisticated ways of capturing and displaying medical image data, such as stereoscopic rendering, animation, and virtual surgery. Nonetheless, there is still a great need for improvements upon such techniques, including improvements in image quality, new ways for users to interact with such images, and greater ease of use of biomedical image display systems.

Current biomedical visualization techniques allow a user to view and manipulate a 3D image of an anatomical object, such as a skeletal structure or an organ. FIG. 1, for example, shows such an image of a skull, formed using such a technique. In that case, the data of the object acquired by the imaging system is typically reconstructed so that the surface of the object is represented as a "mesh" of interconnected polygons; the polygons, which are typically triangles, are defined by a set of interconnected vertices. One well-known technique for generating a mesh to represent the surface of an object is known as the "marching cubes" algorithm, described by W. Schroeder et al., The Visualization Toolkit, Prentice Hall PTR, Upper Saddle River, N.J., 1998, pp.159–64. A high-quality image of the surface of the object requires that the mesh represent the minute topographical details of the surface with high fidelity. The realism provided by current surface visualization techniques is limited by the number of polygons used to form the mesh and the size of the polygons. To increase the accuracy with which very small features of the surface are shown, it is desirable to use a larger number of very small polygons. However, while increasing the number of polygons may provide a more realistic surface, it also tends to drastically slow down the rendering process, particularly rendering in response to user manipulation of the images. As a result of these limitations, current visualization techniques generally cannot provide the amount of surface detail that is desired by medical practitioners. In addition, current techniques tend to introduce artifacts (flaws) into the image during the reconstruction process. For example, one common problem associated with the marching cubes algorithm is that holes or tears can occur in the mesh due to inherent ambiguity in that algorithm. Hence, it is desirable to have an image visualization technique that provides more detailed surface representation with fewer artifacts and which can operate at an acceptable speed using conventional hardware.

One area of advancement in biomedical visualization techniques is virtual surgery. In virtual surgery, a user (e.g., a physician) manipulates a computer input device to define an incision or a cut in a displayed anatomical object. Special-purpose software, sometimes referred to as a virtual cutting tool, allows the user to define the cut and view internal features of the object. Current virtual cutting tools are limited in the degree of realism they can provide. As noted above, one limitation lies in the number of polygons used to represent the surface to be cut. Processing speed requirements tend to limit the number of polygons that can be practically used. In addition, current virtual cutting tools restrict the shape of the cut made by the user to the vertices of the mesh. Hence, both the surface being cut and the cut itself tend to be ragged and/or unrealistic in appearance. Further, such cutting tools often do not accurately depict tissue thicknesses. Therefore, it is desirable to have the virtual surgery cutting tool which provides more realistic visualization of incisions or cuts, without increasing processing power requirements.

Another area of interest is the ability to allow multiple users at different computer systems to collaboratively view and interact with biomedical images in real-time. For example, it is desirable to enable a number of physicians using different computer systems that are remote from each other to view an image of an anatomical object simultaneously; it is further desirable that when one user manipulates the image, the changes are instantly displayed to the other users. Such a system might be used to provide people living in remote rural areas with access to sophisticated medical knowledge, facilities, and techniques, such as are now associated mainly with urban centers. Another field where such capability would be particularly useful is in space exploration. For example, such a system might be used to allow doctors on Earth to interactively diagnose and treat astronauts in a spacecraft or on a future lunar or Martian base.

One major obstacle to accomplishing this is that images tend to require very large amounts of data. Biomedical images in particular tend to be extremely data-intensive in order to provide image quality that is adequate for diagnosis and treatment. Consequently, speedy user interaction with such images tends to require a substantial amount of processing power and sophisticated hardware at the remote stations. Allowing real-time, simultaneous interaction by multiple remote users is considerably more problematic, even with very high-speed communication links. Hence, it is desirable to have a technique for enabling multiple remote users to interact collaboratively with high-resolution medical images in real-time. It is particularly desirable that such a technique not require expensive equipment or inordinate amounts of processing power at each remote station.

SUMMARY OF THE INVENTION

The present invention includes a method and apparatus for enabling a number of geographically distributed users to collaboratively view and manipulate images of an object. A data structure including data representing the object is maintained. The data structure includes a set of variables that are shared by each of a number of remote processing systems. The data structure further includes a number of models of the object, each of which corresponds to a different image resolution. Data is then multicast to each of the remote processing systems based on the data structure, to allow the image to be displayed on each of the remote processing systems. This includes dynamically selecting from among the models of the object. Transmission of user inputs applied at each of the client systems is coordinated, to allow the image displayed on each of the client systems to be updated in real-time in response to user inputs applied at each other client system.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 11A:
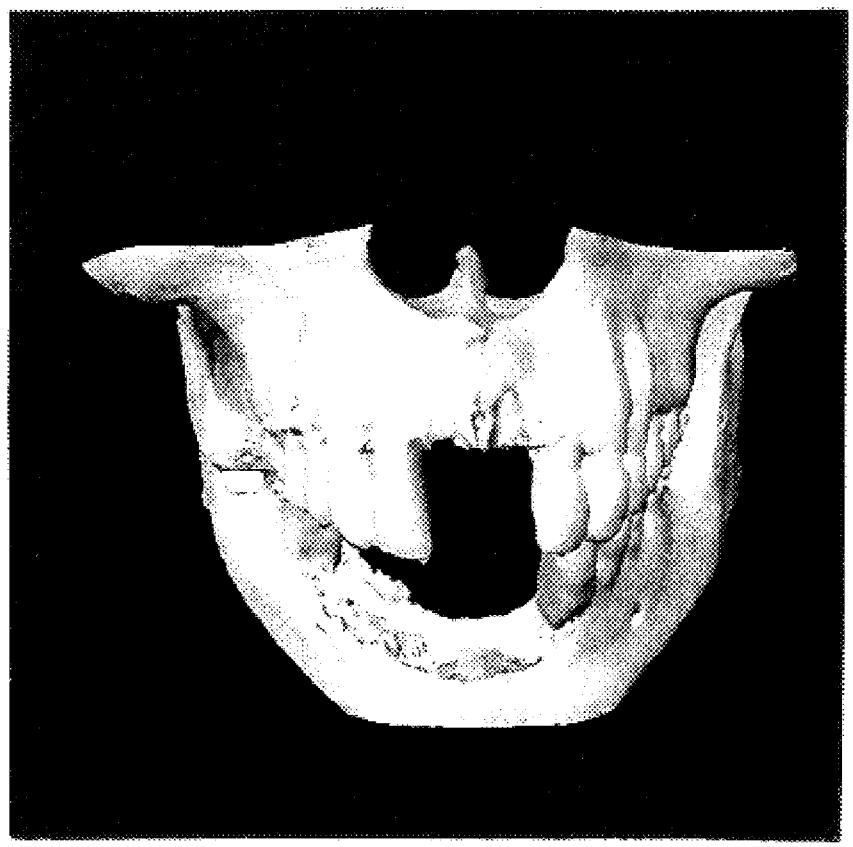
FIGS. 11A through 11D show a sequence of displays associated with the routine of FIG. 10.
Figure 11B:
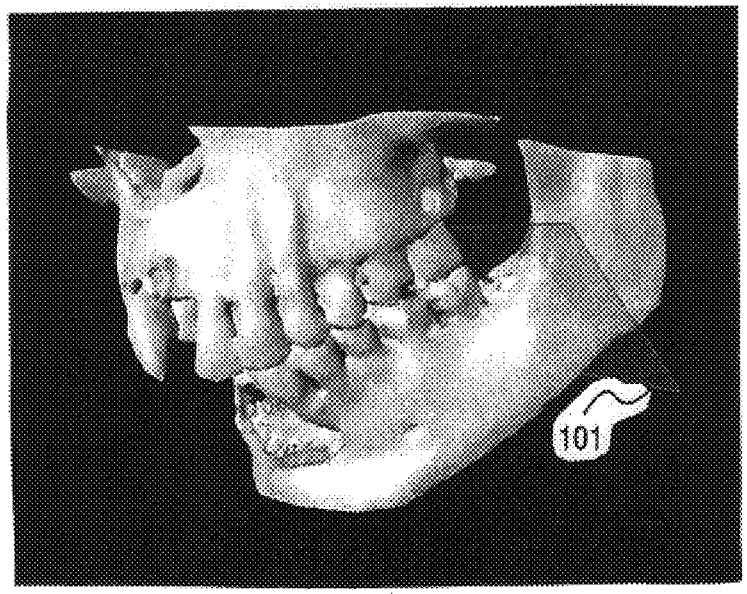
Figure 11C:
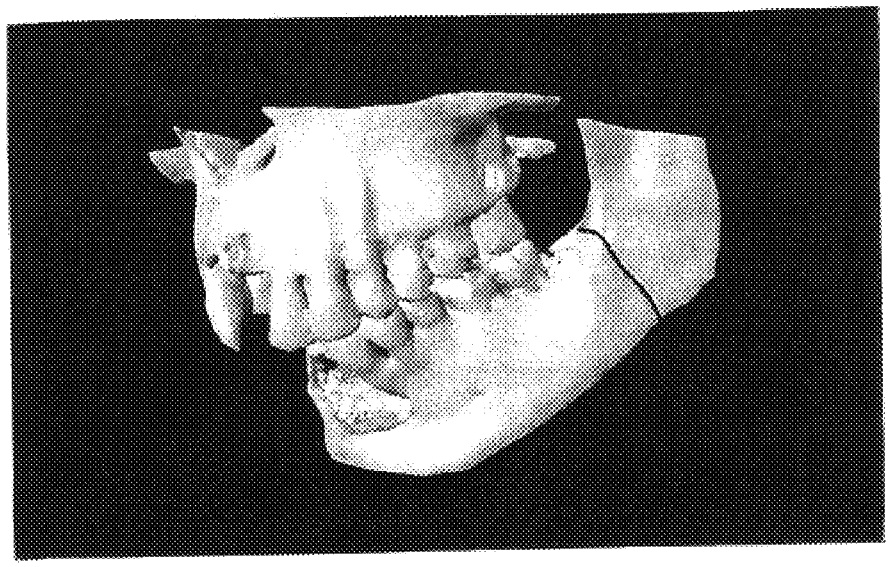
Figure 11D:
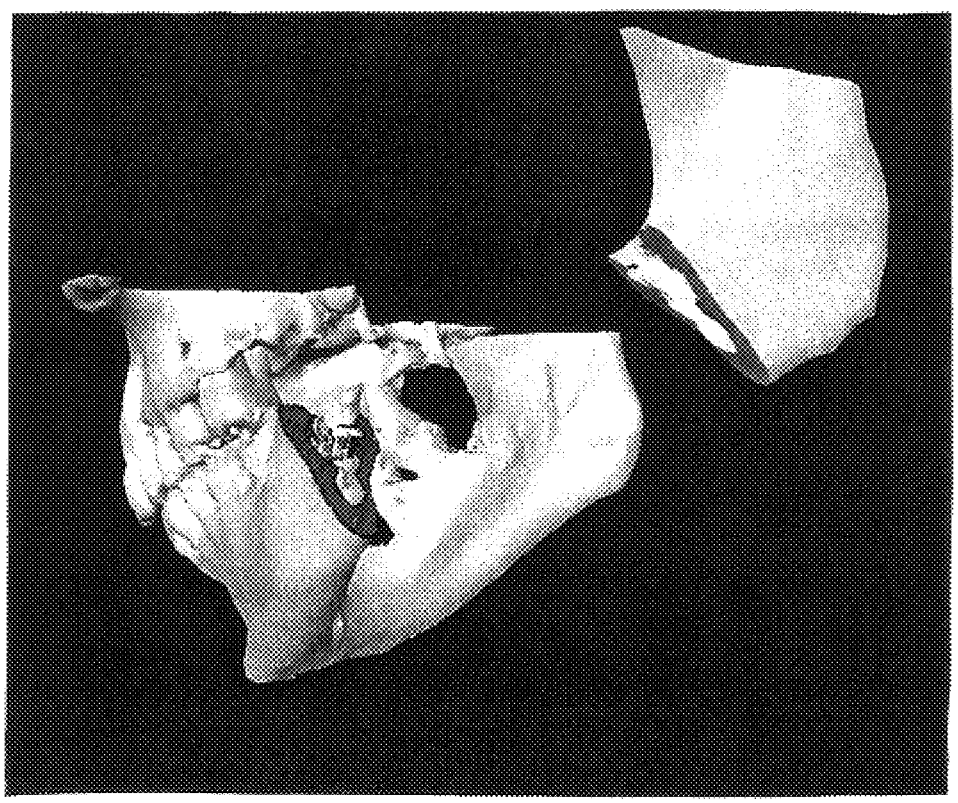
Figure 11E:
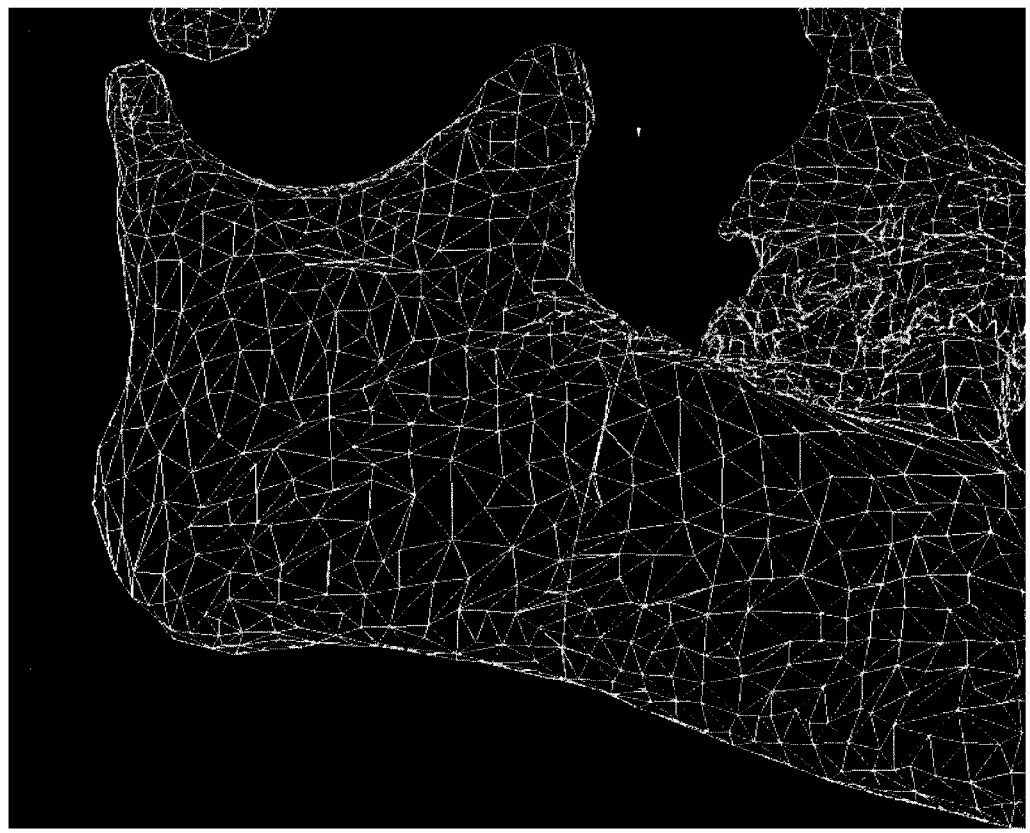
FIG. 11E shows an example of a mesh representing a jaw bone.

A method and apparatus are described for enabling a number of geographically distributed users to collaboratively view and manipulate high-quality, high-resolution, 3D images of anatomical objects based on tomographic data. The method and apparatus are part of a virtual interactive imaging system which, as described in greater detail below, allows the display of high-resolution, 3D images of medical data to a user and allows the user to manipulate the images. The system includes a mesh generation component that generates high resolution meshes to represent surfaces of objects, based on data from a CT or MRI scan or the like. An example of a low resolution mesh is illustrated in FIG. 11E, which shows a mesh representing part of a jaw bone. Using the techniques described herein, meshes are generated so as to avoid tears, or holes, in the mesh, providing very high-quality representations of topographical features of the object, particularly at high-resolution. The system further includes a virtual surgery cutting tool that enables the user to simulate the removal of a piece or layer of a displayed object, such as a piece of skin or bone, view the interior of the object, manipulate the removed piece, and reattach the removed piece if desired. The system further provides a virtual collaborative clinic environment, which allows the users of multiple, remotely-located computer systems to collaboratively and simultaneously view and manipulate the high-resolution, 3D images of an object in real-time. The images may be rendered in four dimensions (4D), wherein the fourth dimension is time; that is, a chronological sequence of images of an object is displayed to show changes of the object over time (i.e., an animation of the object is displayed).

Figure 1:
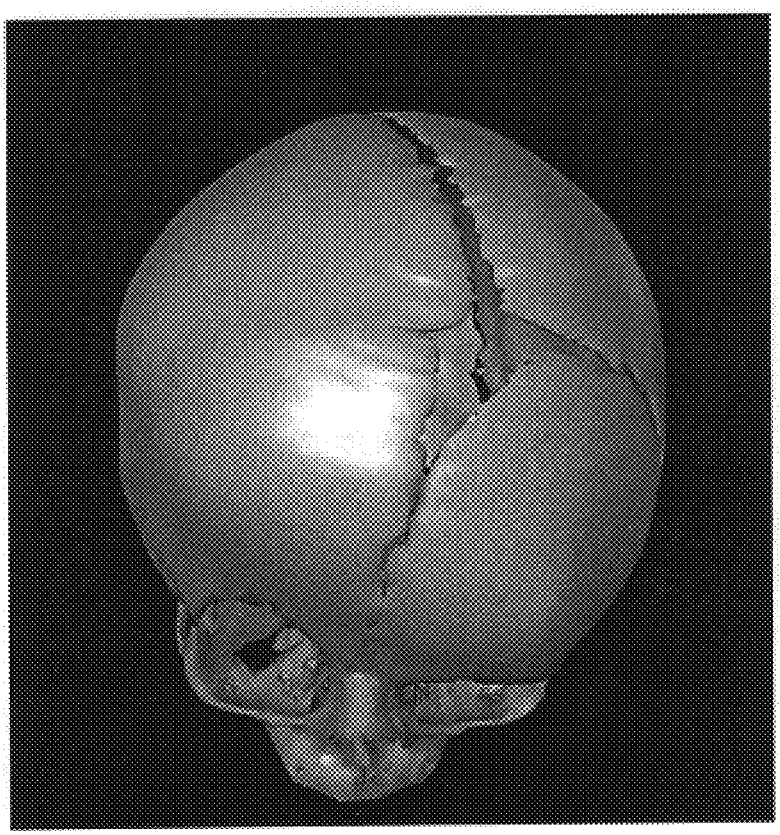
FIG. 1 illustrates a 3-D image of a skull.
Figure 2:
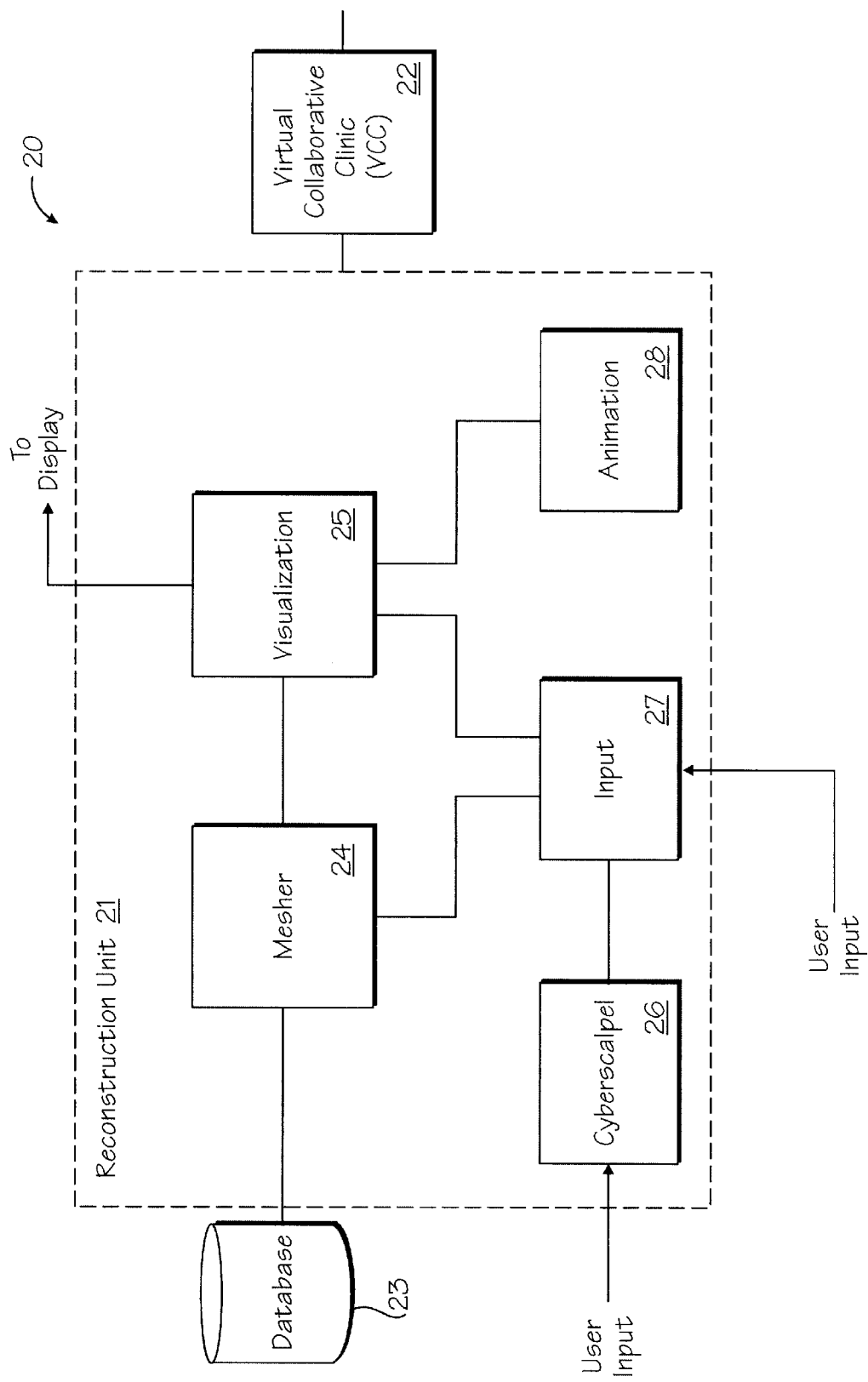
FIG. 2 illustrates a virtual interactive imaging system in accordance with the present invention.

FIG. 2 illustrates an embodiment of the virtual interactive imaging system 20. The imaging system 20 may be embodied as software, which may be written in C, C++, or any other suitable programming language. It should be noted, however, that the imaging system 20 may alternatively be embodied in hardware, or as a combination of hardware and software. Thus, the present invention is not restricted to any particular combination of hardware and or software. The system 20 comprises a core reconstruction unit 21, and a Virtual Collaborative Clinic (VCC) unit 22 that is operatively linked to the reconstruction unit 21. The reconstruction unit 21 accesses medical image data stored in a database 23 for purposes of generating high-resolution, stereoscopic 3-D images. The data may be CT data, MRI data, or any other type of tomographic medical data. Further, the techniques described herein can also be applied to other types of data, i.e., outside the medical field, as will become apparent from the description which follows.

The reconstruction unit 21 includes a mesher component 24, a visualization module 25, a cyberscalpel 26, an input unit 27, and an animation unit 28. The mesher 24 generates meshes to represent object surfaces based on the data stored in the database 23. The visualization module 25 generates images of patient data from medical scans. The cyberscalpel 26 is a virtual cutting tool for virtual surgery which allows the user to simulate cutting of an anatomical object displayed by the visualization module 25, using a conventional user input device. The cyberscalpel 26 is operatively coupled to the input unit 27, which is operatively coupled to the mesher 24 and the visualization units 25. The visualization unit 25 is also coupled to the animation module 28. The user input module 27 receives conventional user inputs for manipulating images and performing other functions, such as may be provided from a mouse, trackball, touchpad, or other standard user input device. The animation module 28 provides the capability to animate displayed images, to show changes to the object over time (4D).

The Virtual Collaborative Clinic (VCC) unit 22 is an extension of the reconstruction unit 21 which enables multiple, remotely located users to interact with the same 3D data set. As described in detail below, the VCC unit 22 may have counterpart components that reside and execute on other, remote processing systems. The VCC unit 22 is designed to allow users at widely distributed locations to view and interact with a common set of 3D objects in a virtual environment, and to share all changes to these objects in real-time. Again, the images may be rendered in 4D in the VCC environment to show changes of the object over time.

The reconstruction unit 21 generally provides ease of use and generality in application. Realistic, 3D stereoscopic images can be produced within minutes from medical scans. High fidelity is a main feature of the software package. It allows surgeons to visualize huge datasets, as from CT scans of patients' faces and skulls, or of the lung or the heart, so that very small defects are noticeable. The visualizations are based on meshes that may use several millions of polygons to describe surfaces. The mesher 24 employs an improvement upon the marching cubes algorithm, as will be described below, which permits polygon reduction without the tearing that is common to marching cubes applications. This approach allows the number of polygons describing surfaces to be reduced drastically (by as much as 98%) without losing topographical features. Polygon reduction permits more effective use of a cyberscalpel 26, so that surgeons can plan complicated surgery ahead of time, using realistic displays.

It should be recognized that, while the embodiments described herein are directed to medical applications, many aspects of the imaging system 20 can be applied outside of the medical field. For example, using features of the imaging system 20, researchers can bisect or otherwise cut into other types of scientific reconstructions, such as geological map of a planet, to gain new insights. Polygon reduction with retention of topography also makes it possible to implement the imaging system 20 on a PC, so that stereoscopic, 3D visualizations can be manipulated in real-time on an inexpensive computer. A main benefit is to enable visualization and interaction with patient-specific data in an immersive, virtual environment, which may be PC-based. Such PC-based systems can be placed on spacecraft.

Figure 3:
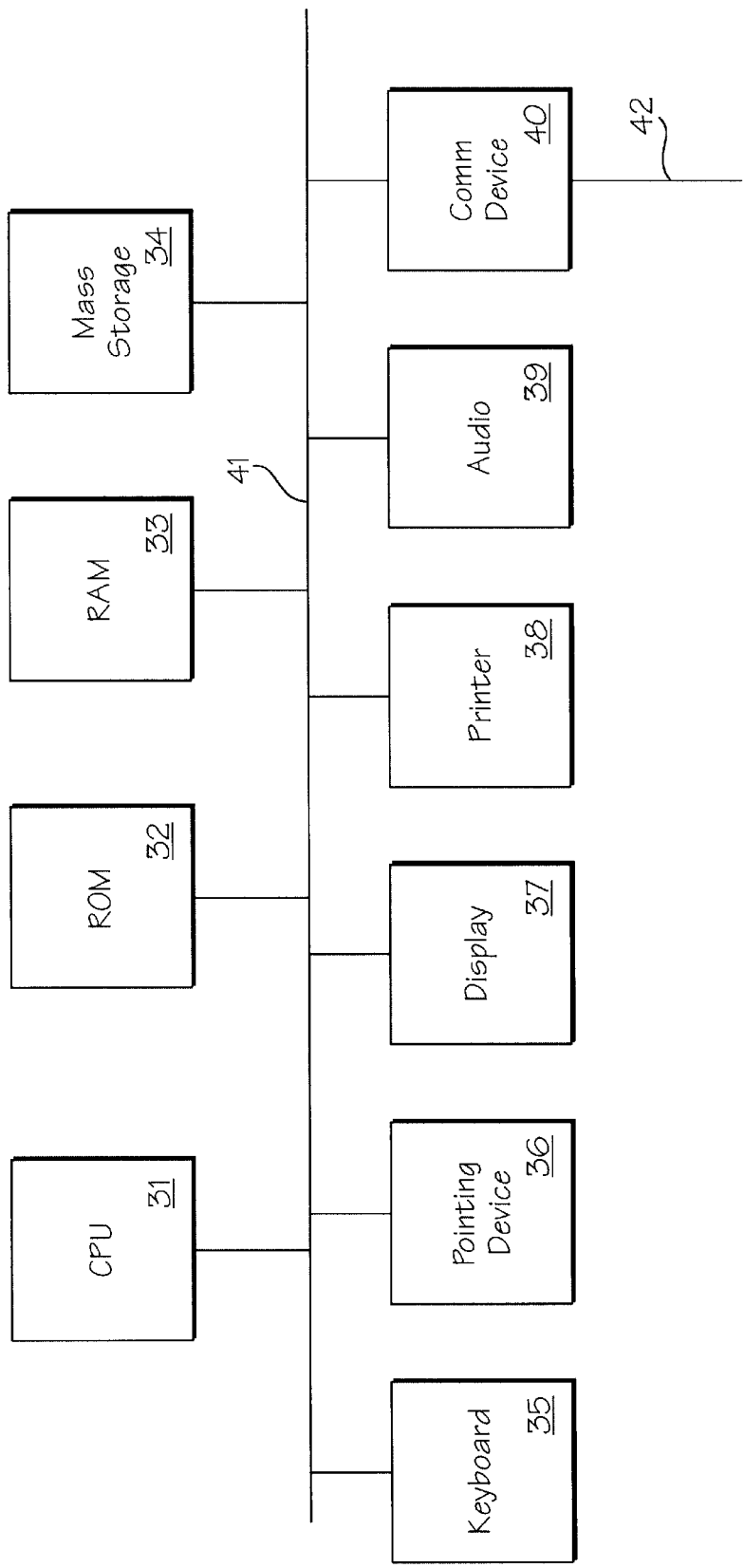
FIG. 3 shows a block diagram of a hardware platform that may be used to implement the virtual interactive imaging system.

As noted above, the imaging system 20 may be embodied as software that can be implemented in a conventional PC; however, the imaging system may also be implemented on a workstation, or any other suitable platform, or it may be distributed across two or more processing systems on a network. FIG. 3 illustrates one example of a hardware platform which may be used to implement the imaging system 20. Note that FIG. 3 is a high-level conceptual representation that is not intended to be limited to any one particular architecture. The illustrated hardware platform includes a central processing unit (CPU) 31, read-only memory (ROM) 32, random access memory (RAM) 33, and a mass storage device 34, each connected to a bus system 41. The bus system 41 may include one or more buses connected to each other through various bridges, controllers and/or adapters, such as are well-known in the art. For example, the bus system 41 may include a system bus that is connected through an adapter to one or more expansion buses, such as a Peripheral Component Interconnect (PCI) bus. Also coupled to the bus system 41 are a keyboard 35, a pointing device 36, a display device 37, a printer 38, and audio output subsystem 39, and a communication device 40.

The pointing device 36 may be any suitable device for enabling a user to position a cursor or pointer on the display device 37, such as a mouse, trackball, touchpad, stylus, a microphone combined with an audio input system and speech recognition software, etc. The display device 37 may be any suitable device for displaying alphanumeric, graphical and/or video data to a user, such as a cathode ray tube (CRT), a liquid crystal display (LCD), or the like, and associated controllers. Mass storage device 34 may include any suitable device for storing large volumes of data, such as a magnetic disk or tape, magneto-optical (MO) storage device, or any of various types of Digital Versatile Disk (DVD) or compact disk (CD) storage. The communication device 40 may be any device suitable for enabling the hardware platform to communicate data with another processing system over communication link 42, such as a conventional telephone modem, a cable television modem, an Integrated Services Digital Network (ISDN) adapter, a Digital Subscriber Line (XDSL) adapter, a network interface card (NIC) such as an Ethernet adapter, etc. The audio subsystem 39 may include, for example, an audio sound card and a speaker. Of course, many variations upon the illustrated architecture can be used consistently with the imaging system 20 described herein.

I. MESHER

The mesher 24 (FIG. 2) operates based on segmentation to provide surface information, and automatic registration followed by mesh generation to describe the surface(s). The mesher 24 generates surface models of 3D objects imaged in a volumetric data set. The mesher 24 is similar to existing surface generation tools, except as otherwise described herein. Although the mesher 24 is not restricted to medical datasets, a more advantageous use of this application is thought to be in the generation of surface models of anatomical objects from CT and MRI medical data and the like. Typical models include the surface of the skin and skull on patients requiring reconstructive surgery and the surface of the heart for patients undergoing bypass graft surgery. The method is tailored to the kinds of contour data provided from the source.

Figure 4:
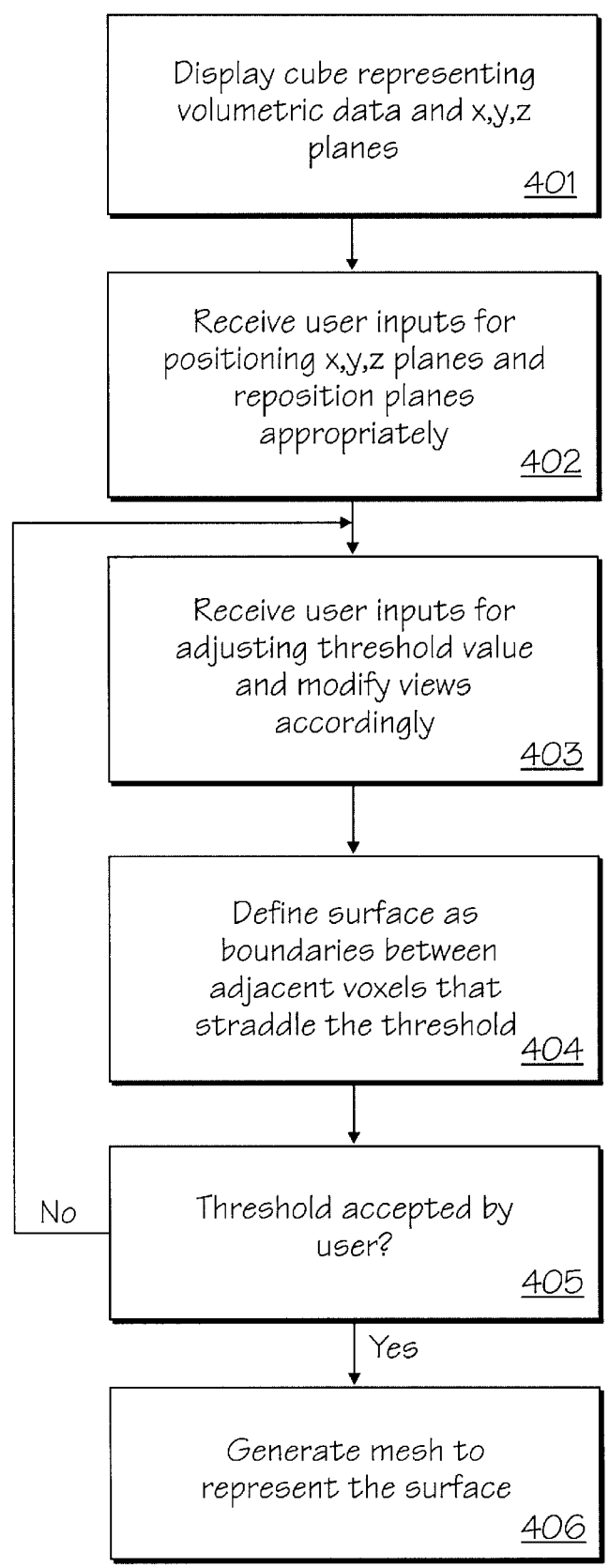
FIG. 4 is a flow diagram illustrating a user interactive process for configuring the virtual interactive imaging system for mesh generation.
Figure 5:
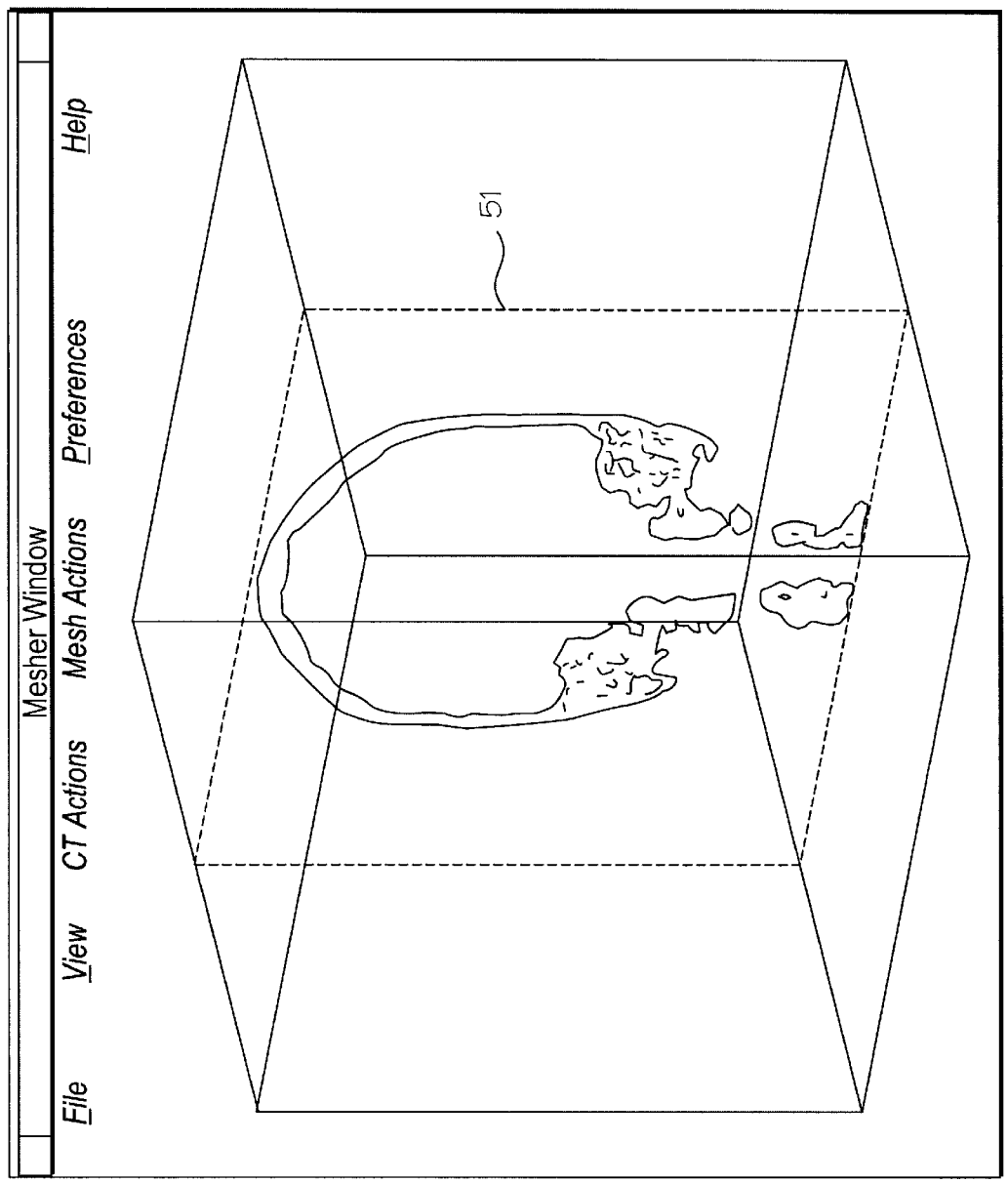
FIG. 5 illustrates an example of a display presented to user during execution of the routine of FIG. 4.

FIG. 4 illustrates a user-interactive process performed by the imaging system 20 in connection with mesh generation. The user interface to the mesher 24 provides an efficient means of interacting with the volumetric data to set parameters necessary for the mesh generation. A key parameter is the threshold, which determines what portion of the data will constitute the surface boundary. Accordingly, at block 401 the user is presented with a graphical window depicting the volumetric data as an outlying cube, as illustrated in FIG. 5. This cube may be manipulated by the user with a mouse (or other user input device) to an arbitrary orientation on screen.

Three planes corresponding to the x, y, and z planes of the data volume, an example of which is shown as plane 51, are positioned by the user to intersect the data volume. At block 402, the user places each plane at the desired location along its corresponding axis and displays the two-dimensional data associated with the intersection of the volume. Next, at block 403 the user adjusts the threshold value by moving a slider bar or other similar control. To view the threshold data for a desired plane, the user selects a check box for that plane. The threshold value for each plane initially may be set to a predetermined default value, so as to represent bone, for example. To facilitate the user's selection of the boundary threshold, the display in each plane shows only those pixels whose value is: 1) equal to the threshold value and to 2) have at least one adjoining pixel with a value lower than the threshold value. The purpose of this operation is to display only the outline that will constitute a surface boundary, and not display any of the internal volume of the object. Every voxel in the volumetric dataset is classified as above or below this threshold, and at block 404 the surface is interpolated to be the boundary between adjacent voxels that straddle the threshold. If the user accepts the current threshold setting at block 405, then at block 406 the mesher 24 generates a mesh to represent the surface using the current threshold setting. Otherwise, the routine repeats from block 403, where the user selects another threshold value.

Figure 6A:
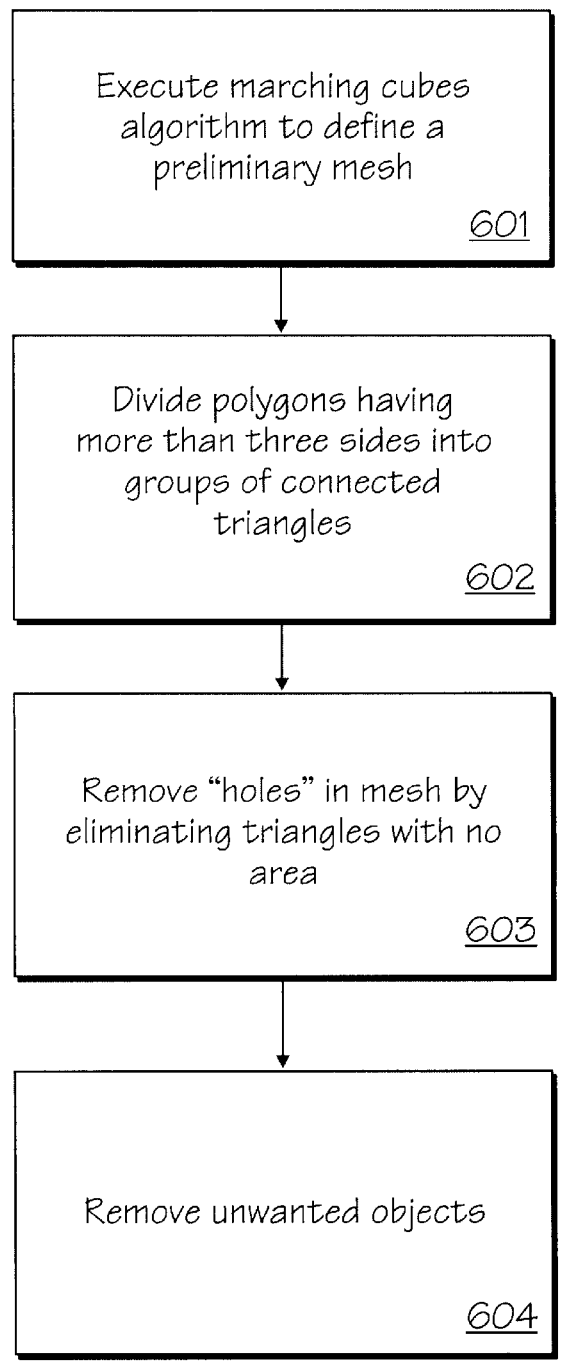
FIG. 6A is a flow diagram illustrating a process for generating a mesh to represent the surface of an object.

FIG. 6A illustrates the process for generating the mesh (block 406) in greater detail, according to at least one embodiment. Initially, at block 601 the points that constitute the above-noted boundary are connected into a triangle-based mesh using the marching cubes algorithm. The marching cubes algorithm produces a mesh consisting of a mixture of polygon shapes. However, the mesher 24 performs additional operations to produce a more regular, triangle-based mesh from the marching cubes generalized polygon mesh. An example of such a mesh is provided in FIG. 11E, which shows part of a mesh representing a jaw bone. The procedure includes dividing the polygons which have more than three sides into groups of connected triangles at block 602. Hence, the mesher 24 closely approximates small changes in curvature of the object as it re-generates the mesh. The resulting more regular, triangular mesh leads to greater coherency in the surface structure and a more realistic representation of the data.

Figure 6B:
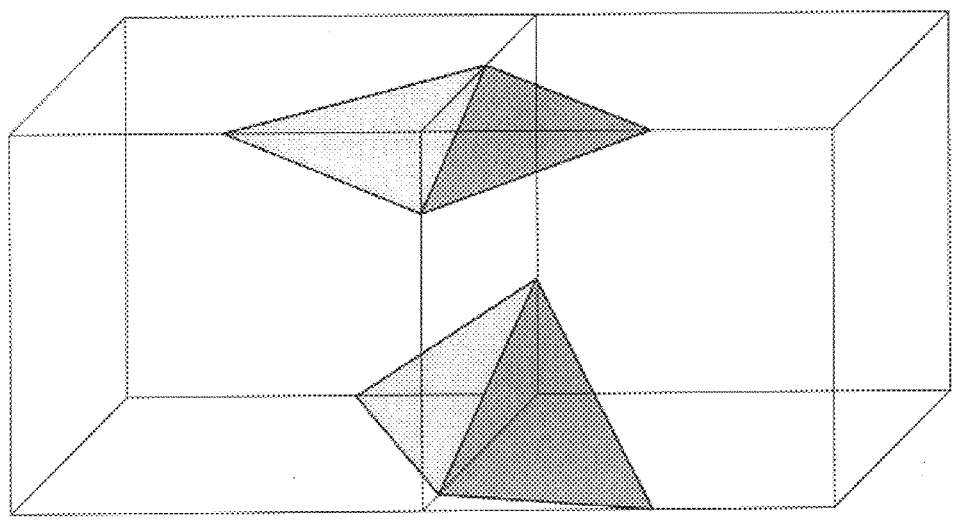
FIG. 6B illustrates a portion of a mesh which is properly constructed, such that the mesh no holes.
Figure 6C:
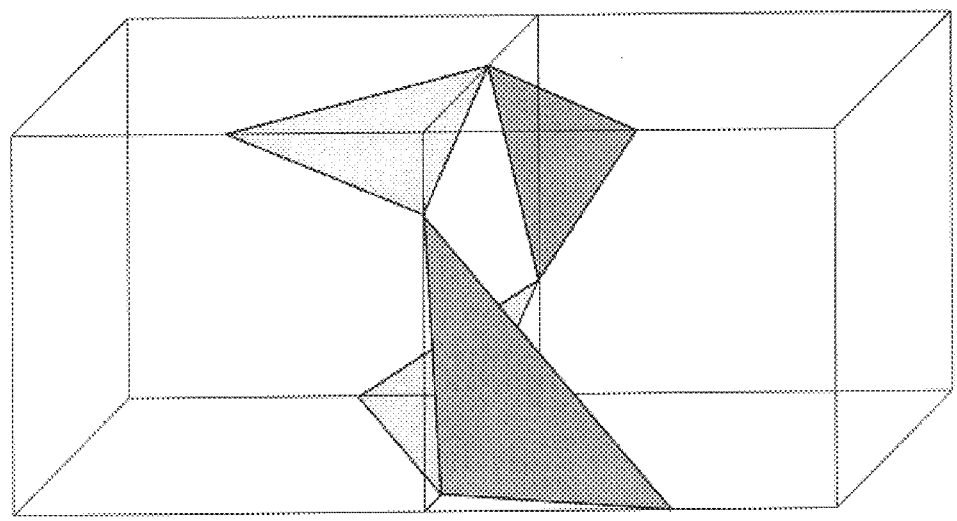
FIG. 6C illustrates a portion of a mesh that is improperly constructed, such that the mesh has a hole.

At block 603, all triangles with no area (i.e., triangles for which two or more vertices lie on top of one another) are eliminated—this step prevents tearing (occurrence of holes) and spurious surfaces in the model during subsequent operations on the mesh. Such tears are common to 3D reconstructions that are based on the marching cubes algorithm alone. FIG. 6C illustrates an example of a portion of a mesh that has a hole, as often results from using the marching cubes algorithm alone. Note that the triangles in the left and right cubes connect the intersections on their shared face in a different way, such that they do not share edges. The result is a single surface that contains a hole. In contrast, FIG. 6B illustrates an example of a portion of a mesh that has no holes. Note that the triangles in the left and right cubes connect the intersections on their shared face in the same way, such that they share edges. The result is two discrete surfaces that do not contain any holes. Hence, the present technique for surface generation allows for generation of meshes that may be reduced greatly without losing surface integrity or topography. Retention of surface integrity and topographical features is important for implementation of interactive tools such as the cyberscalpel 26 (FIG. 2), since the quality of the initial model is propagated throughout subsequent operations on the data.

Generation of a surface mesh tends to produce many distinct objects bounded by a surface. In general, only a few of these objects are of interest, and the others constitute artifacts produced by noise found within the volumetric data. Accordingly, as a final step in the mesh generation process, such unwanted objects are removed at block 604.

Once the mesh is generated, the visualization module 25 takes over. The visualization module 25 has features to permit greater versatility in viewing the images. The main functionalities of the visualization module 25 include three display modes for viewing 3D models: 1) wire frame, 2) gourad shading, and 3) semi- to full-transparency of selected objects. The visualization module 25 also provides for interactive manipulation of objects with the mouse (or other user input device), such as rotation, translation, and zoom; objects can be turned off or cut into any direction by arbitrary cutting planes.

The animation module 28 provides for animations by saving key frames in sequence to create an animation file. These animations are viewable on many platforms, including the monitor screen, and can be videotaped.

One significant feature of the mesher 24 is that it was designed to use the maximum range of gray levels present in the data, rather than resampling the data to fit a standardized range. A typical standardized range of gray levels is 8 bits in length, allowing 256 distinct gray levels, whereas raw CT data are 12 bits, or 4096 distinct gray levels. Retaining the higher resolution in the volumetric data provides a smoother surface reconstruction (a finer-grain image) that leads to improved realism in visual appearance.

II. CYBERSCALPEL

The cyberscalpel 26 uses a mesh that is reduced from its original million or more polygons (as generated by the mesher 24) to a number more practical for speedy interaction with a cutting tool. Retention of geometry during mesh reduction is essential to implementation of interactive tools, since the goal is virtual surgery that is reasonably accurate in detail. The QSlim program from Carnegie Mellon University can be used to perform mesh reduction, and is believed to yield excellent results in either Unix or NT based operating systems. Mesh reduction can alternatively be performed as a reduction in the number of vertices based on minimization of the local mesh curvature. In at least one embodiment, the mesh is reduced to 50,000 polygons, which is far in excess of that used by many who are developing tools for virtual surgery. Thus, the imaging system 20 permits use of higher fidelity 3D reconstructions than do other packages, producing a more realistic image for interaction when preparing for surgery or when learning new procedures.

Figure 7:
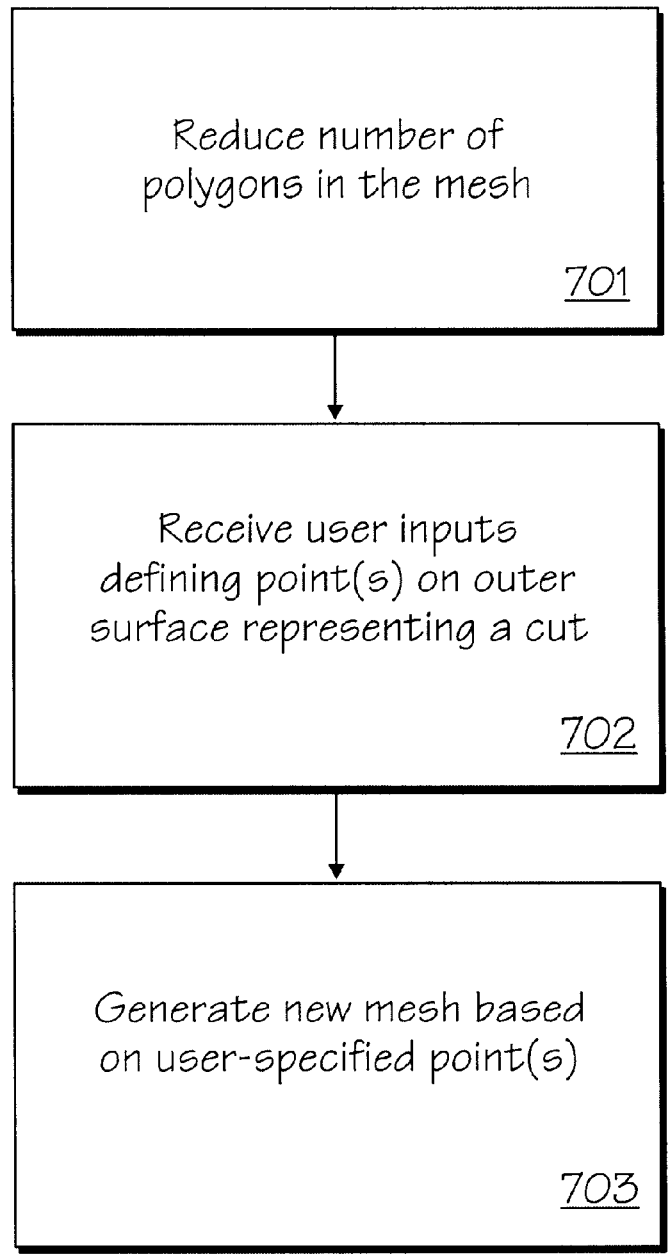
FIG. 7 is a flow diagram illustrating an overall process associated with operation of the virtual cutting tool.
Figure 9A:
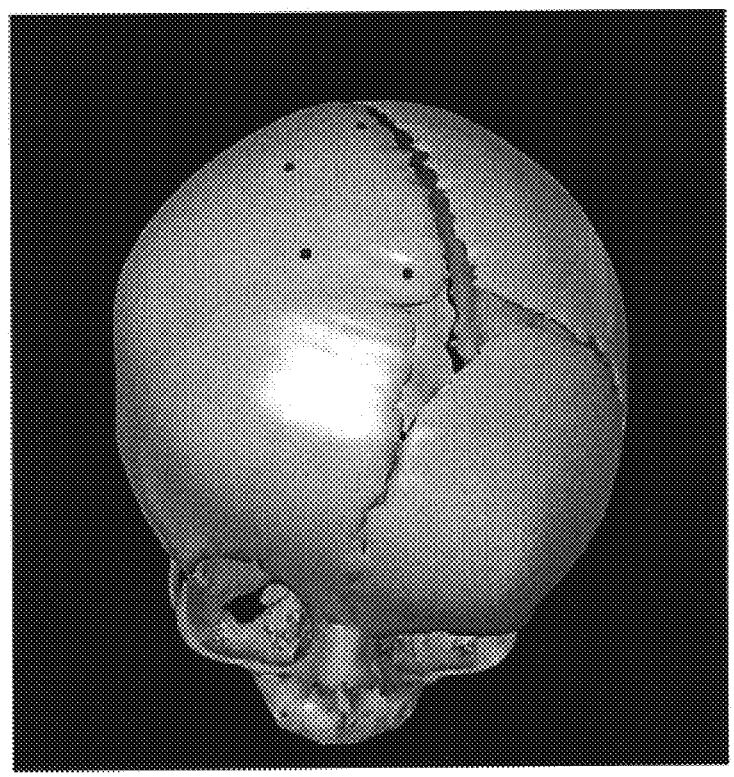
FIGS. 9A, 9B, 9C and 9D illustrate displays showing a process of removing a section from a skull using a virtual cutting tool.

Refer now to FIG. 7, which shows an overall process associated with operation of the virtual cutting tool. Prior to initiating virtual surgery, the number of polygons in the mesh is reduced at block 701, using techniques such as those mentioned above. At block 702, the cyberscalpel 26 is invoked, receiving user inputs defining one or more points representing a cut on the outer surface of the displayed object. The user inputs may be entered from a conventional user input device, such as a mouse. For example, in one embodiment the operator decides where a cut should begin and how it should extend along the external surface of the object. Points are placed by the user on the surface of the object using the mouse (or other pointing device) one after another until the cut is outlined. FIG. 9A illustrates an example of four user-defined points (dark dots) placed on the top of a skull image, using this technique. FIGS. 9A, 9B, 9C and 9D illustrate steps in the process of removing a section from a skull using the cyberscalpel 26. At block 703, the cyberscalpel 26 generates a new mesh based on the user-specified points.

Figure 9B:
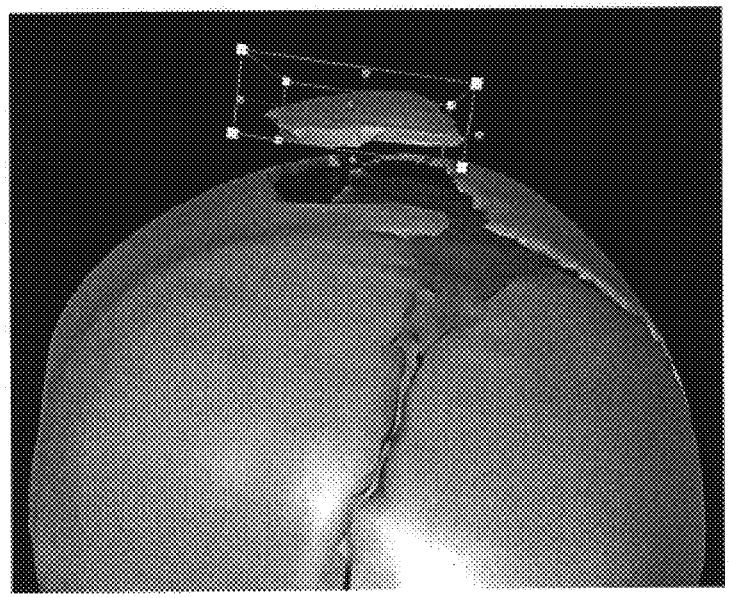
Figure 9C:
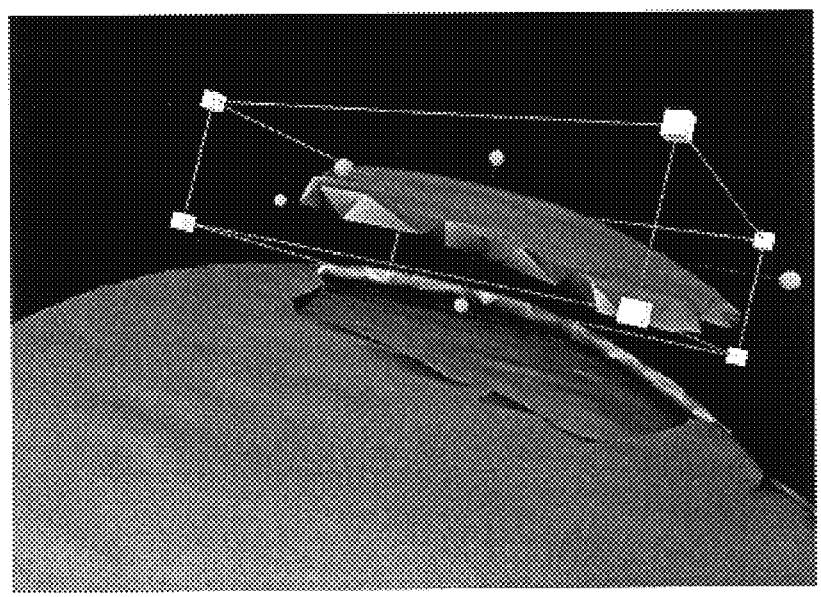

Two different virtual cutting techniques are implemented by the cyberscalpel 26, as a result of differences in the geometry of bones and other tissues and organs of the body. For cutting flat bones such as those of the skull, the object is visualized as a shaded solid, as shown in FIGS. 9A, 9B and 9C. The underlying mesh is not visible. Although only the external surface is apparent to the viewer, the inner surface is also reconstructed.

Figure 8:
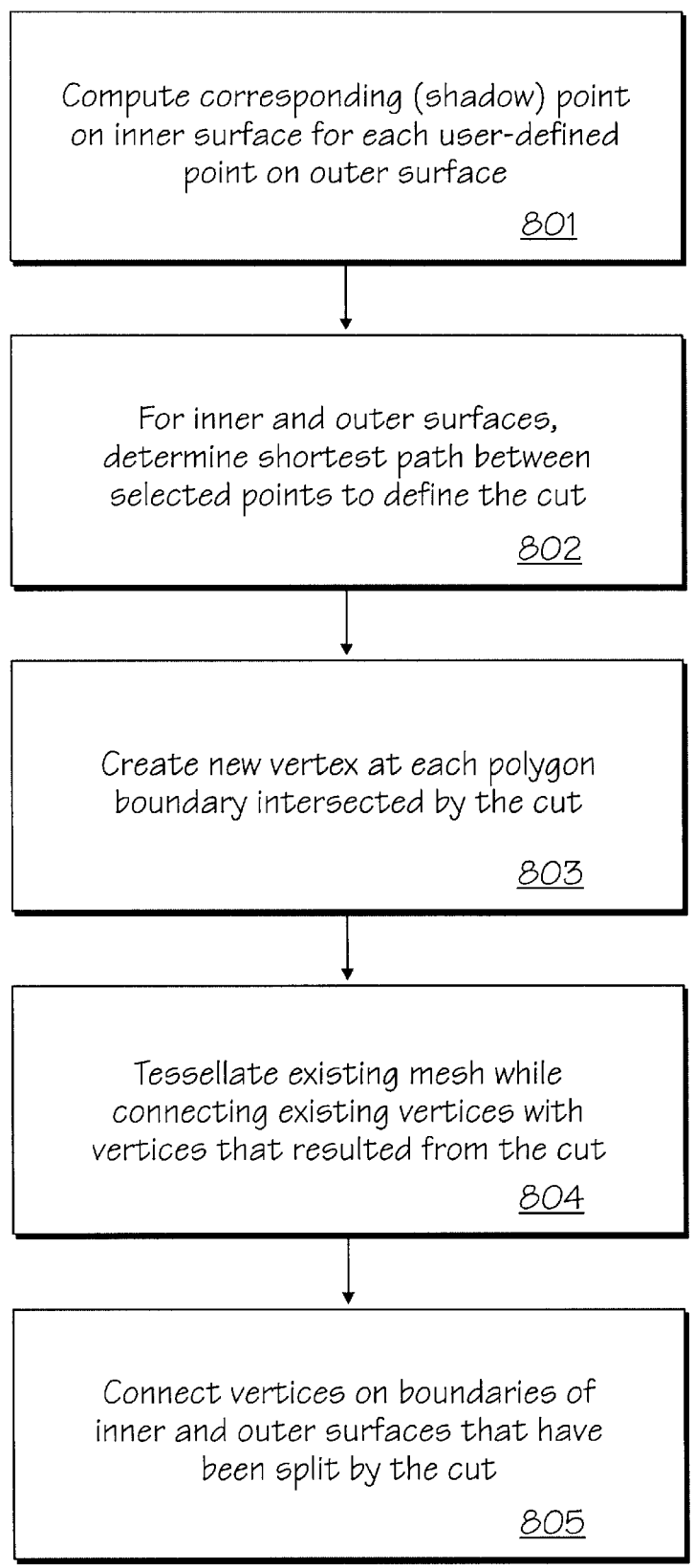
FIG. 8 illustrates a process associated with the virtual cutting tool, for use with flat bones such as the skull.

FIGS. 8 illustrates a process performed by the cyberscalpel 26 for flat bones, such as the skull. At block 801, as the user defines points on the outer surface of the object (see FIG. 9A), simultaneously points on the inner surface, which shadow those on the external surface, are automatically identified. The points on the surface of the object need not be placed close together. At block 802, an algorithm determines the shortest path between the selected locations and logically defines the shape of the cut. At block 803, while following along the path from one selected location to the next, a vertex is created at the edge of each polygon that is intersected by the path between successive points. Next, at block 804 the existing mesh is tessellated (tiled with polygons) as the original vertices are connected with the new vertices, i.e., the vertices which resulted from cutting.

Figure 9D:
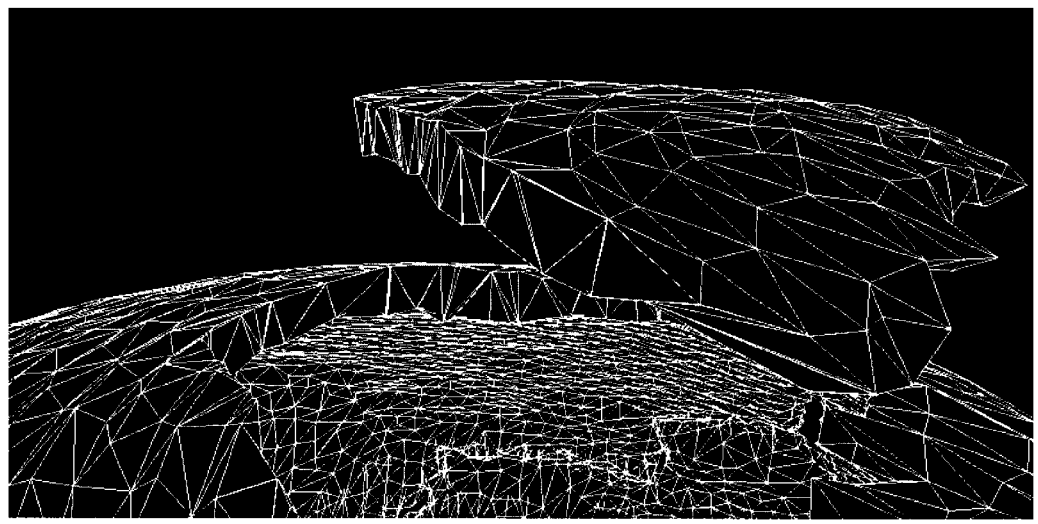

At block 805, vertices on the boundary created by the cut on the inner surface are connected with vertices on the boundary created by the cut on the outer surface, so that the segmented piece appears as a 3D solid when manipulated—that is, the thicknesses of the layers cut into are visible. This effect can be seen in FIGS. 9B, 9C, and 9D. FIG. 9B shows a display frame with a piece being removed from the skull based on user-defined points. FIG. 9C shows a display frame with a magnified view of the removed skull piece of FIG. 9B. FIG. 9D shows another magnified view of a removed skull section, in which the polygons of the mesh are visible, including triangles created to connect the inner and outer surfaces of the skull. This feature provides for a more realistic, 3D segment of bone to be cut from the original reconstruction and manipulated. The removed piece may be outlined by a set of "handles" by which the user can manipulate the removed piece or reattach it to the main object. Examples of such handles are shown in FIGS. 9B and 9C as the points connected by lines around the removed piece of skull.

Using this technique, in contrast with prior virtual surgery tools, points to be connected are not necessarily existing points of the mesh. In addition, in contrast with prior techniques, the vertices at the boundary of the cut are connected.

In an extension of the above technique, the user simply drags a scalpel-like instrument along the surface of the image, and new points (as well as new polygons) are established precisely along the path.

Figure 10:
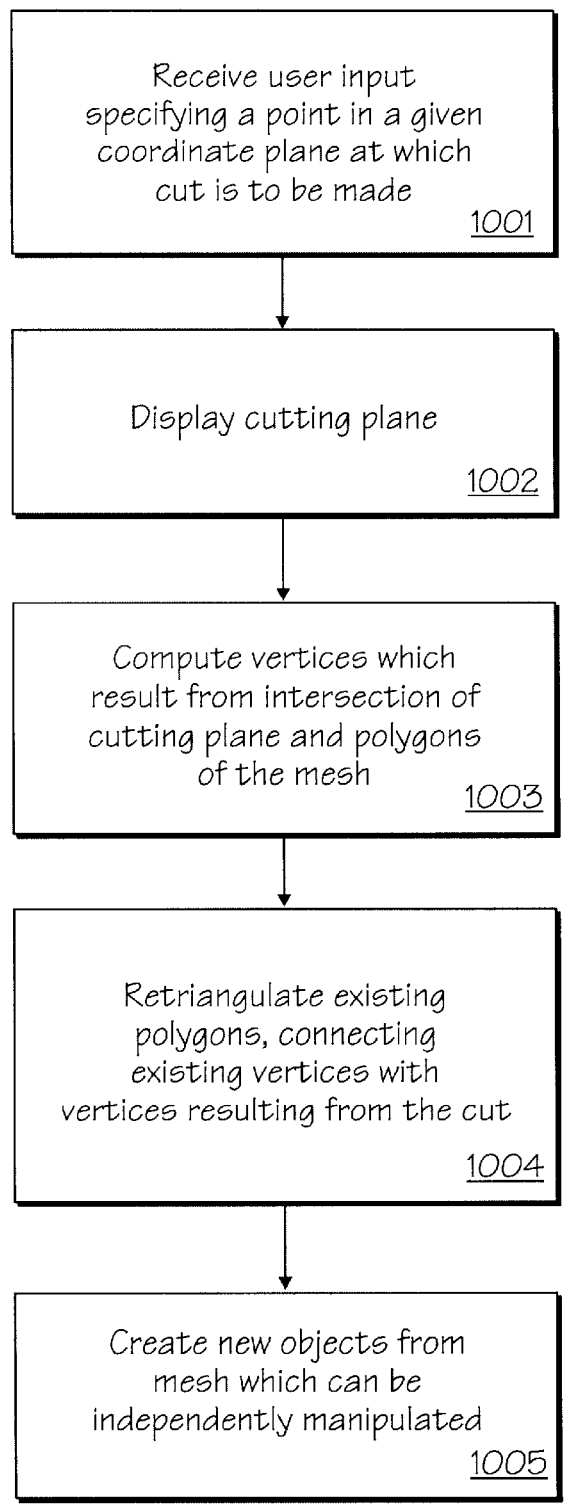
FIG. 10 illustrates a process associated with the virtual cutting tool, for use with the jaw or other non-flat bones.

For the jaw, a variation of this technique is employed. This is because the jaw has an outer, U-shaped surface as well as other corresponding inner surfaces that are, however, more irregular. Again, polygon reduction to 50,000 polygons is performed. FIG. 10 shows a process used by the cyberscalpel 26 for cutting the jaw, according to at least one embodiment. FIGS. 11A through 11D illustrate an example of what may be displayed to the user during this process. FIG. 11A shows a frontal view of a jaw prior to the cutting process. Referring to FIG. 10, at block 1001, a location is selected by the user about midway on the external surface of the jaw (in this example), where the cut is to be made. At block 1002, a cutting plane 101 is then displayed as intersecting the object at this user-selected location, as shown in FIG. 11B. At block 1003, an algorithm computes vertices which result from the intersection of the polygons' edges with the cutting plane. Another algorithm retriangulates the existing polygons at block 1004, connecting existing vertices with vertices created by cutting. The cut is represented by a line along the virtual jaw to assist in placement of the cuts before separation of the objects, as shown in FIG. 11C. At block 1005, an algorithm then separates the mesh into connected components, creating new objects, which can then be manipulated independently, as shown in FIG. 11D. As with the flat bone embodiment of the cyberscalpel (described above), vertices on the cut edge of the inner surface are connected with vertices on the cut edge of the outer surface, so that the removed piece appears as a 3D solid.

As many cuts can be made as are needed to capture the surgical procedure realistically. Manipulation of the plane and subsequent objects may be facilitated by the use of the Open Inventor toolkit, available from TGS of San Diego, Calif., or any other suitable software. Note that, as with the mesher 24, these techniques employed by the cyberscalpel 26 are not limited to use on the skull or the jaw, nor to anatomical objects generally.

Several extensions to the above-described techniques can also be implemented. For example, the cyberscalpel 26 may provide the capability for the user to reposition the separated components more easily in three-space, in order to properly represent the original geometric structure. This embodiment, a series of visualization workstations that are linked together via a network. The number of workstations is essentially unlimited. The system includes at least two visualization workstations (i.e., VCC clients for displaying the data) and an information server that mediates the transmission of variables between the clients. Optionally, the information server may reside within one of the visualization workstations. The VCC component 22 may implement the functionality of either the VCC client, the information server, or both.

The visualization workstations are not tied to any specific hardware, but in at least one embodiment, are based on the OpenGL graphics API of Silicon Graphics Inc. of Mountain View, Calif., which is available on a wide variety of computer platforms. Network connectivity is also independent of hardware—however, the network protocols for TCP/IP (Transport Control Protocol/Internet Protocol), UDP (User Datagram Protocol), and Multicast UDP are supported. The VCC accommodates different levels of hardware resources.

Figure 12A:
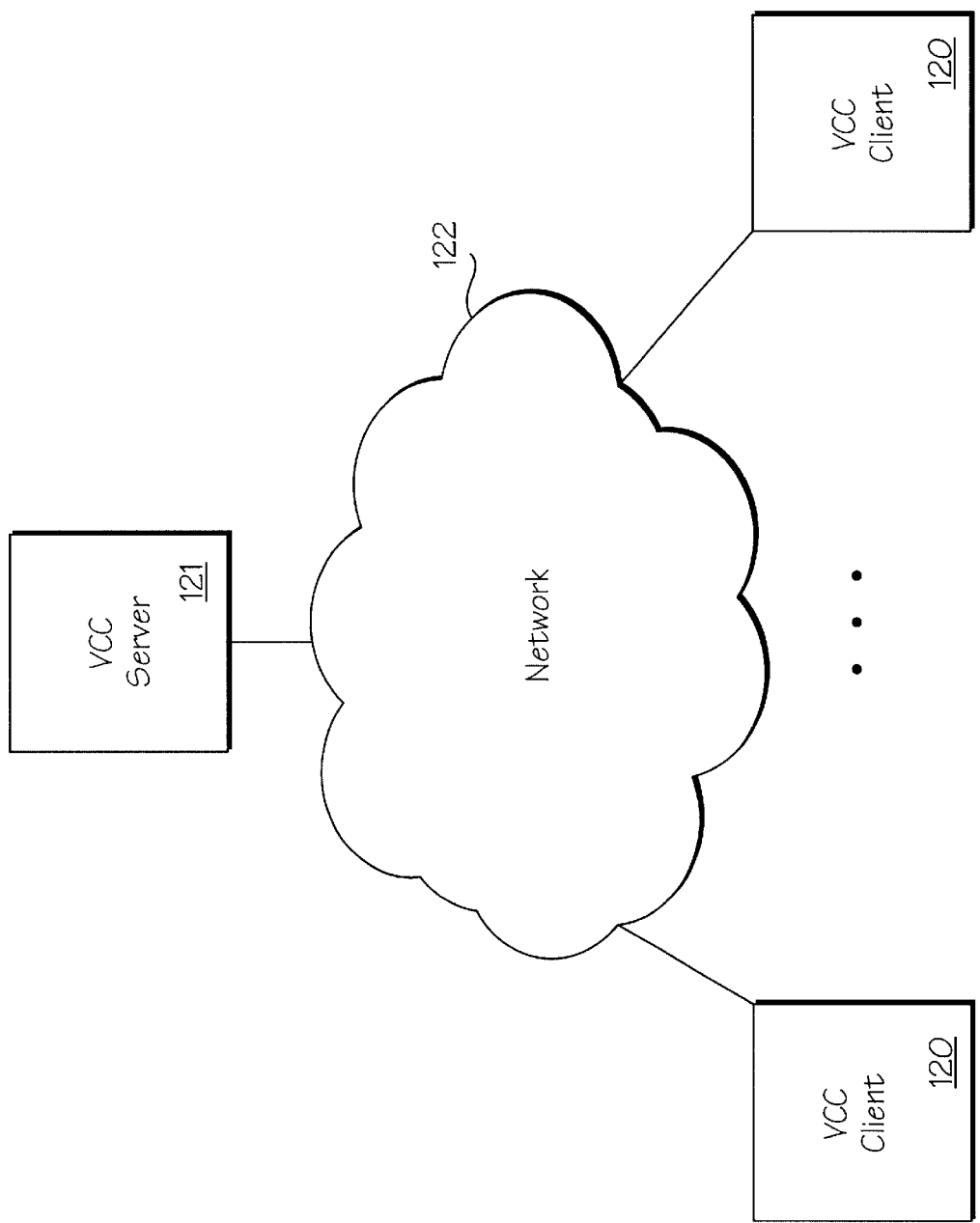
FIGS. 12A and 12B show two different network configurations associated with the Virtual Collaborative Clinic (VCC)
Figure 12B:
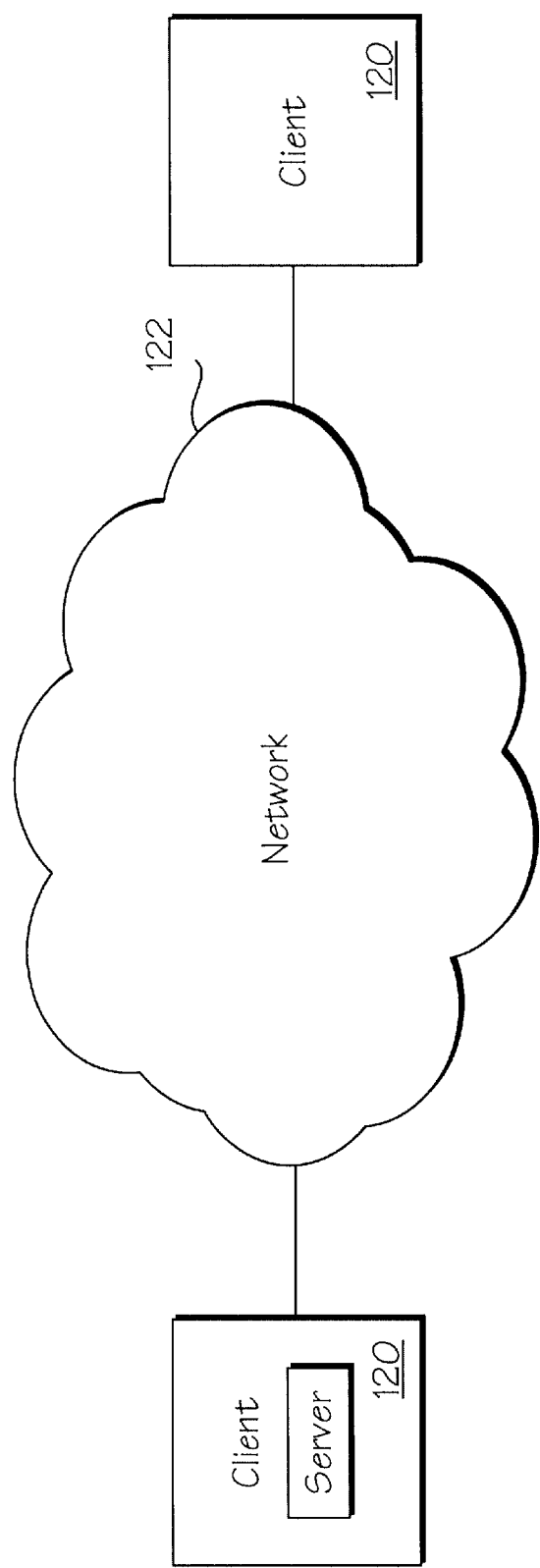

Referring to FIG. 12A, the users of two or more client computer systems 120 may collaboratively interact with a displayed 3D object via a network 122. Interaction is coordinated by the information server 121 on the network 122. As noted, the information server may reside within one of the visualization workstations, as shown in FIG. 12B. The client systems 120 may be conventional PCs, for example. The server 121 may also be a PC, although in other embodiments, the server 121 may be a workstation, or a high-end graphics supercomputer, as described further below. The clients contact the information server via an IP address across the network 122, but they are not required to be able to contact one another.

The VCC 22 described herein is particularly significant to the telemedicine arena, in which the space and humanitarian aspects of the can be done by maintaining in memory the original geometry of the removed segment(s). The original geometry can be viewed as a semitransparent object, much like a ghost of the part, so that replacement bones can be repositioned within the ghost very easily. Computational restoration of the overlying and underlying tissues is desirable here, so that the result of the operation can be viewed in advance. In addition, the cyberscalpel 26 may be linked with other algorithms to provide structural and spatial coordinate information about the separated components. This information can be used as a template, which the user can use when harvesting bone from other sites or when fabricating implants. In the case of the jaw, replacement bones may come from the fibula. The fibula can be reconstructed with the segments of bone from a representative jaw surgery placed above it. The fibula can then be segmented, using the angles of the cuts and lengths of the segments as templates. The replacement segments can then the replaced to redefine the jaw.

III. VIRTUAL COLLABORATIVE CLINIC (VCC)

The VCC component 22 (FIG. 2) is an extension of the reconstruction unit 21 that generates a virtual environment (the "VCC environment") that enables multiple users to interact in real-time with the same stereoscopic 3D data set. One advantageous use for such a system is to examine 3D reconstructions of medical data for consultation and diagnosis by medical practitioners who are located in different parts of the world. Thus, the VCC environment is particularly suited to displaying 3D models of anatomical reconstructions used in medical diagnoses and treatment planning, and the collaborative aspects allow physicians at different geographical sites to manipulate these objects as though looking at a common display.

In brief, the VCC architecture is comprised of, in at least one applications are of enormous significance. When spacecraft are well on their way to Mars, it will be nearly impossible to send astronauts back to Earth for treatment. Development of a virtual environment, imaging and the force-feedback (haptic) devices and technologies will make it possible to send sonically scanned data back to Earth for visualization, when necessary. The method of treatment can be devised by an expert on Earth and put into a virtual environment mode. The virtual environment images can be communicated to the spacecraft (with minutes of delay, of course), where the visualizations can be replayed in virtual environment or can be used to drive a slave robotic device. An astronaut physician can thus be walked through a procedure, and can practice it in virtual environment, before working on the ill member of the team. In addition, the VCC 22 can be used to bring medical services to people in remote or poverty stricken areas. The VCC environment provides capabilities for information sharing for collaboration, as well as data manipulations at each client site, independent of other sites. In addition, the VCC environment may include graphics service from a graphics supercomputer, as described below.

The VCC provides several features to provide the remote interaction capabilities. In at least one embodiment, each computer in the collaboration contains a copy of the 3D reconstruction to be viewed, and has the graphical and computational capabilities to display such an object. Collaboration occurs by linking together the attributes of the object (i.e., location, orientation, color, etc.) on each computer so that a change to an attribute on one computer is immediately propagated to all the other participants' computers. Functionally, this system allows an individual to manipulate an object in space and show a particular aspect of the model to the other participants, as though they were all looking at a common screen. A pointer is programmed into the software, permitting a participant to point out salient structures to others as a discussion takes place.

Implementation of the VCC environment may be hindered on any one or more of the client computers 120, due to limitations in the computational and/or graphical capabilities of such client computer(s), particularly if such client computers are lower end PCs. However, the prevalence and relatively low cost of PCs (in comparison to other platforms) makes it desirable that the VCC component 26 run on PCs, so a large degree of scalability is provided. Multiresolution representations of the mesh models are used in the VCC environment to accomplish this. For example, by switching to a low resolution version of a model (for example, a model having 1/50 of the triangles in the full model) during user interactions, the manipulation of an object takes on a real-time quality which allows the user to precisely position an object by hand. Upon completion of the manipulation, a high resolution version of the data is displayed, causing a slight delay but not interfering with the users actions, since the object is no longer being manipulated.

There may be situations in which the display of the high resolution data on a PC is simply not practical, because the dataset is so large that it could take minutes to render the image. Extending the idea of multiresolution display, the VCC described herein allows a graphics supercomputer to render a stationary, high resolution dataset, and to distribute the images to all of the participating client sites as their high resolution display. Using the capabilities of a high-bandwidth network such as the Next Generation Internet, a technique for real-time capture and transmission of images from the graphics supercomputer may be implemented. As described further below, this implementation uses a muiticast distribution method to send the images out to all the client sites, allowing a server to provide images for potentially hundreds of client sites simultaneously. A key benefit of this component is the elimination of the need for high speed graphics systems at the client sites, allowing an institution to leverage a single high speed graphics system through their organization.

Figure 13:
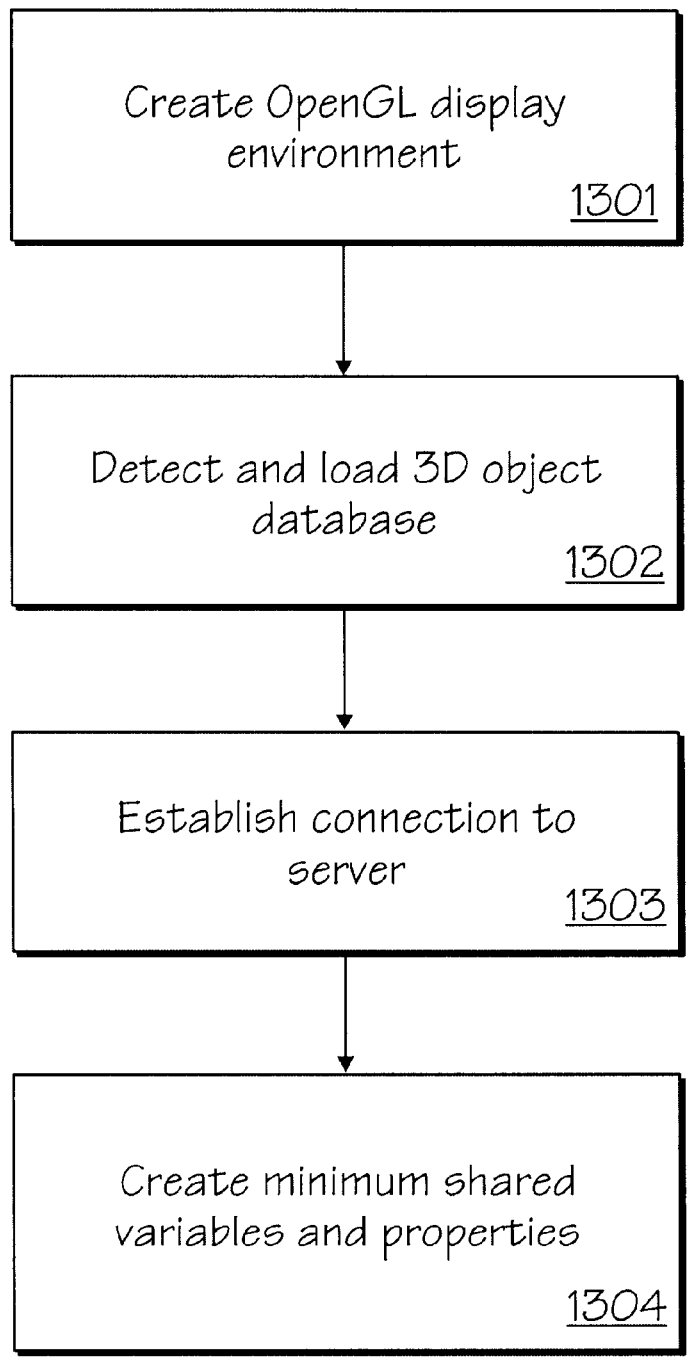
FIG. 13 is a flow diagram showing a process for initiating the VCC environment.

The first step in launching the VCC environment is to start the information server. This is a discrete piece of software from the VCC itself, and may be left running as a service on a machine assigned as the information server. At least one embodiment, the information server is the World2World toolkit of SENSE8 Corporation of Mill Valley, Calif. FIG. 13 illustrates the procedure for starting the VCC application.

On startup, the VCC component 22 implementing the client application performs the following procedure. At block 1301, an OpenGL display environment is created. At block 1302, the 3D object database is detected and loaded. At block 1303, a connection to the information server is established. A block 1304 the minimum shared variables and properties are created. In at least one embodiment, the minimum shared variables and properties are: 1) location and orientation of the camera (users viewpoint) in the virtual environment; 2) lighting applied to the scene; 3) name of the current object to display; and 4) name and state of any devices (i.e., the mouse or a third tracking device) connected to the workstation. If another client has already created any of these variables on the information server, the server associates the corresponding variables and properties between client sites.

The general operation of the VCC environment is as follows. Upon successful startup of the client, the user may load one of the 3D objects in the database into the viewing environment via a menu selection. Once an object has been selected, the name of the object is sent via the information server to all the other clients and triggers a load of the same object at each client site. If the object is not available in a particular client's database, a simple shape (e.g., a cube) is loaded to indicate failure to find the desired object. The failure is also signaled to the information server, which then requests that the originating client sends the object data to the clients that do not already have it.

Each object is embedded in a scenegraph, which is an organizational tree used to store all the properties of the object, such as geometric information about the object, spatial orientation, lighting conditions, colors, etc. Each scenegraph is analyzed as it is loaded, and all the variables and properties in the scenegraph (except the geometry itself) are created as shared variables and linked through the information server. Modification of any property due to scene manipulation is then automatically propagated to all the other clients, providing the collaborative aspect of the system.

Click-and-drag mouse operations or similar operations using other peripheral devices are used to perform spatial manipulation of the scene. Modifications of properties, such as color or opacity, are performed via menu operations and dialog boxes. When a user loads a new object, all of the shared variables associated with the old object scenegraph are destroyed and replaced by those in the new scenegraph.

Handling of the shared variables within the VCC is independent of the information server. Within the VCC client, a transmission queue is created that holds information that must be sent to the information server. Modification of a shared variable cause the variable and its new value to be placed in the queue, where it is held until the transmission function is executed. The transmission function gathers all the variables in the queue and sends them as a list having entries in the form (variable, value) to the information server for redistribution. Any server system that can handle data of this form may be used as the information server—examples are Microsoft's DCOM, Sun's Java Shared Data Toolkit, or the World2World toolkit from Sense8. A timer is used to trigger when the transmission function is executed—for example, transmission every 50 milliseconds may be suitable.

The display routines of the VCC are compatible with different hardware having vastly different graphics performance. The general technique is referred to as multi-resolution display. In essence, several representations (models) of each 3D object are created, each model having an order of magnitude less geometry components than the last. All of these models are stored in the scenegraph, and the VCC chooses one of them to display based on a series of pre-set criteria. One such criterion is response time to user manipulations. For example, rotations of an object by dragging the mouse should produce a smooth, animated sequence of rotations that track the users movements in real time. However, another criterion may be object detail when the object is static, provided the user does not have to wait too long for the static image to be rendered. As noted above, displaying one of the lower resolution images during scene manipulation and then displaying a higher resolution image when stopped accomplishes these goals. Providing information to the VCC about the graphics capability of the specific hardware at a client site allows the system to choose the appropriate levels of detail for these operations. Thus, different users linked in the VCC collaboration may be looking at the same object, but at different levels of detail, especially during manipulations. Note that this is the main reason behind sharing all of the information in the scenegraph except the geometry.

Figure 14:
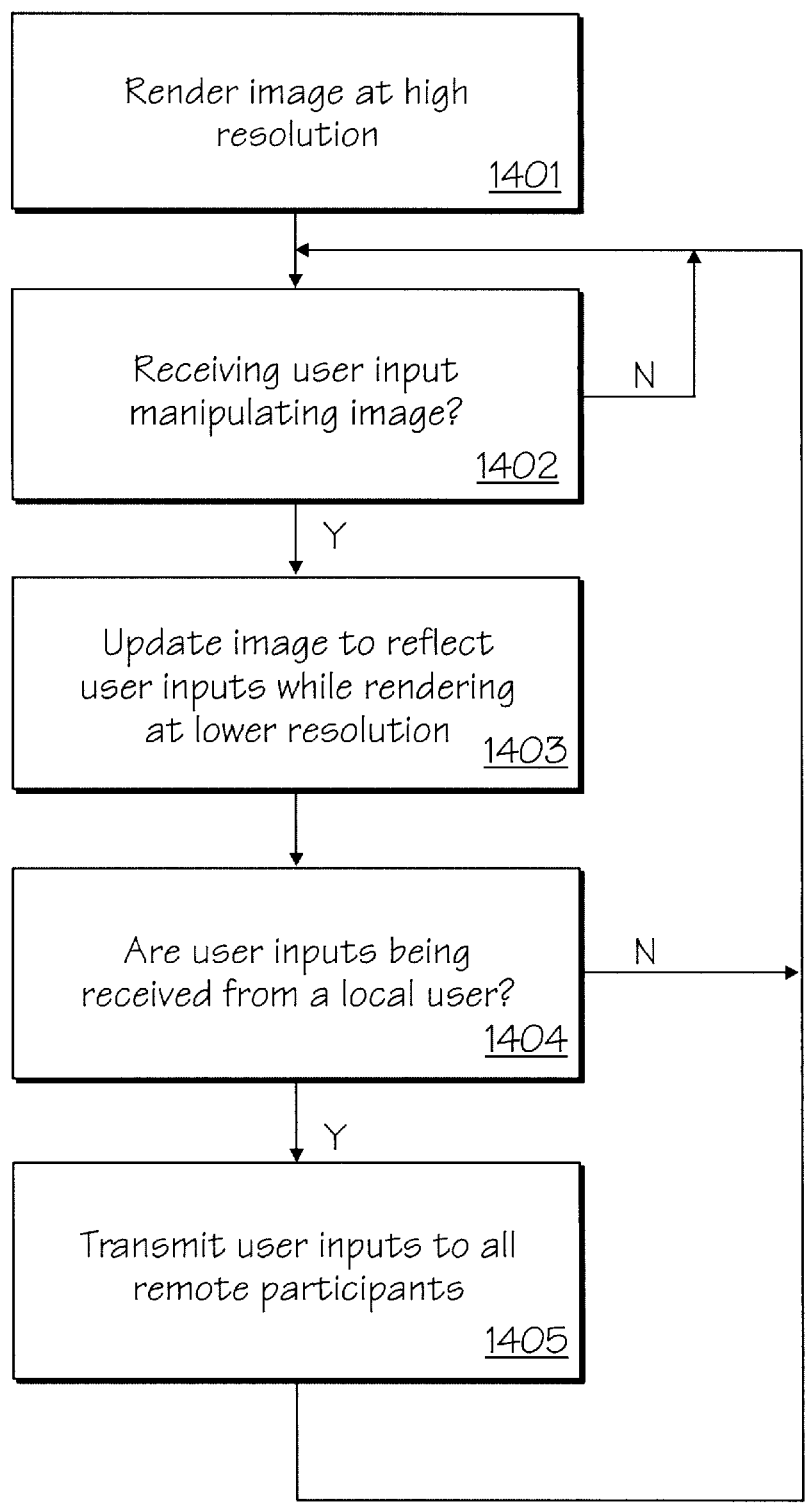
FIG. 14 is a flow diagram showing a process for implementing multiresolution display for the VCC environment.

FIG. 14 illustrates an embodiment of the multiresolution display process. At block 1401, the image is rendered on a client system statically at high resolution. If the user input for manipulating the image is received at block 1402, then at block 1403, the displayed image is updated to reflect the user input (i.e., rotation, translation, etc.) while being rendered at a lower resolution (based on the appropriate model in the scenegraph). If, at block 1404, the user inputs are being received from a local user, then at block 1405, shared variables representing the user inputs are transmitted to the remote participants.

Figure 15:
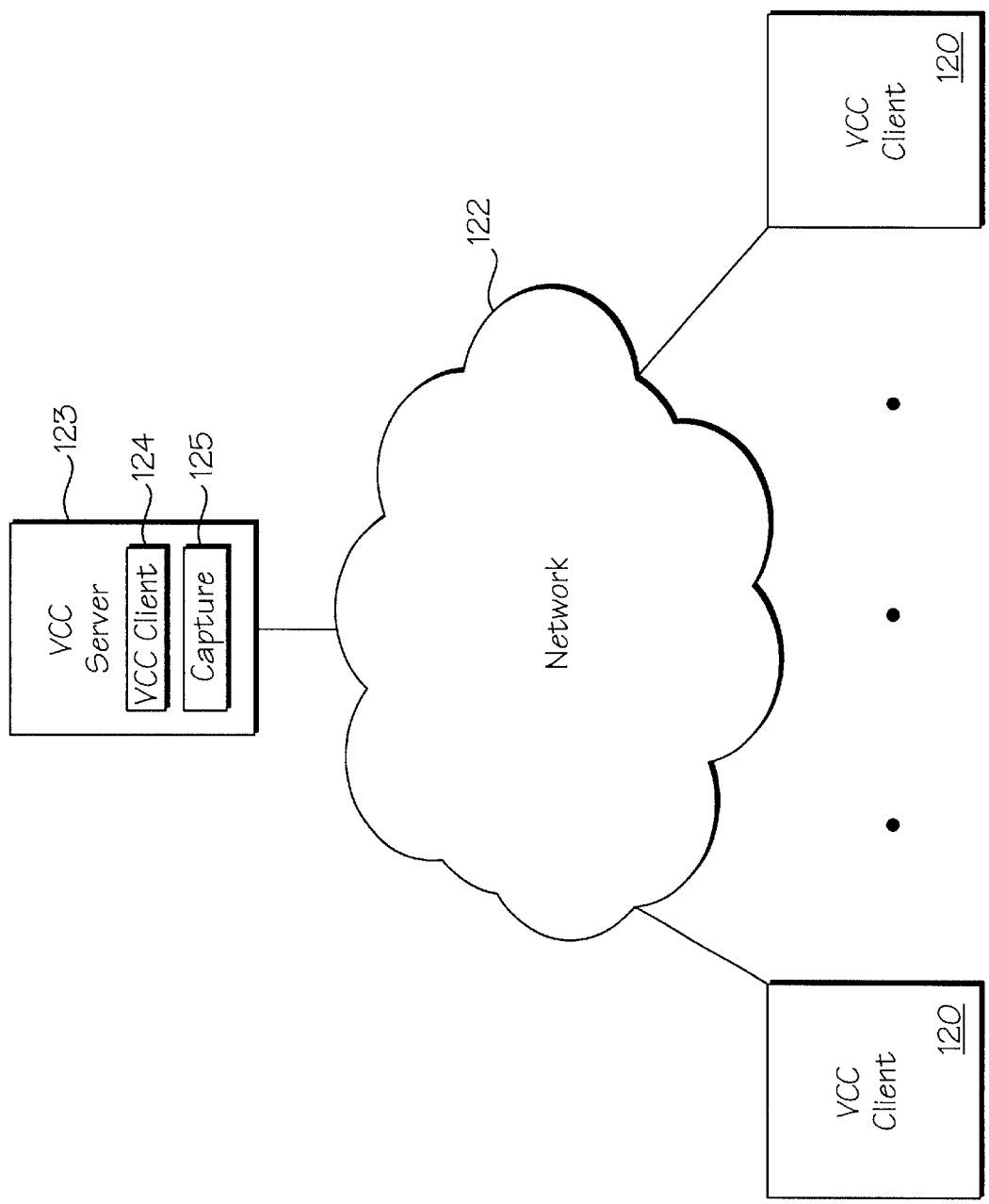
FIG. 15 shows a network configuration for an embodiment of the VCC that includes a graphics supercomputer.

Optionally, the VCC environment may include a graphics supercomputer server. The purpose of such an embodiment is to leverage the speed of a graphics supercomputer for very large (i.e. highly detailed) objects that would not be renderable on a PC desktop system. An example of such an embodiment is illustrated in FIG. 15. In this example, the network 122 is a high-bandwidth network between all clients 120 participating in the collaboration. The graphics server 123 runs a client application 124 identical to that of the VCC client systems 120, but also contains a capture process 125 designed to capture the image created by the display system and transmit it to the VCC client systems 120. Upon reception of the image from the graphics server 123, the VCC clients 120 display this image rather than generating their own through the local display system. In at least one embodiment, the graphics server 123 is an Onxy2 system with InfiniteReality2 graphics, from Silicon Graphics Inc.

The graphics server process operates in two modes: 1) continuous transmission of images, akin to streaming video, and 2) single-frame transmission in response to an event in the program. Mode "1)" is used if the VCC clients are not expected to perform any local rendering. Mode "2)" is used if the VCC clients are expected to render the low resolution images during manipulation of the object, but receive the high resolution static display from the graphics server.

Figure 16:
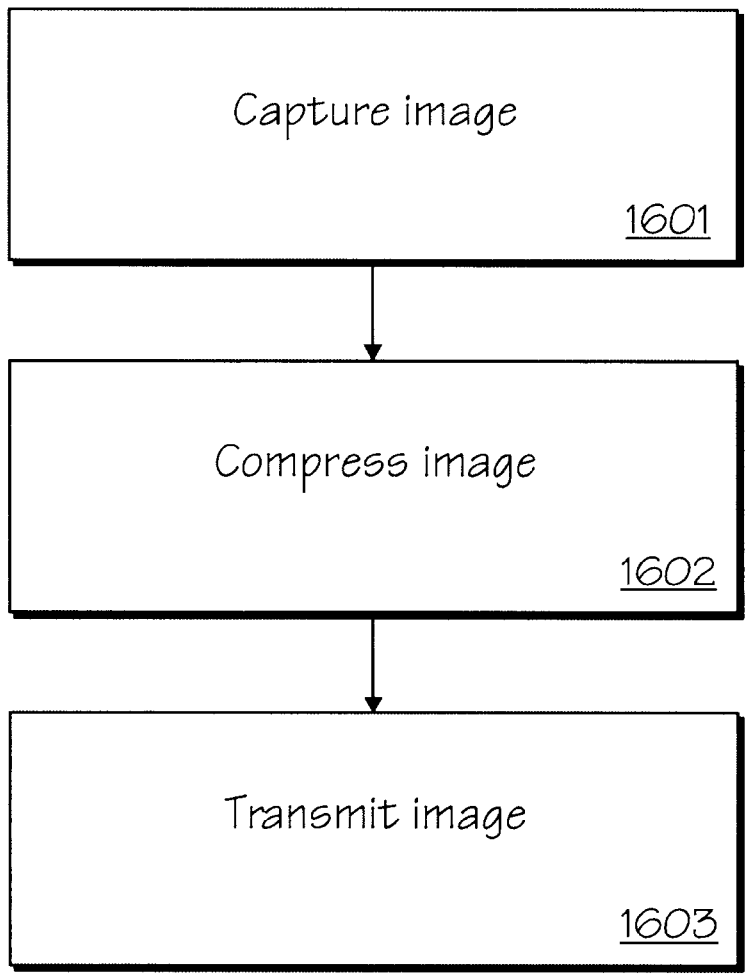
FIG. 16 is a flow diagram showing the overall process implemented by the graphics supercomputer of FIG. 15.

The overall operation of the graphics server process is described now with reference to FIG. 16. At block 1601, the image is captured from the OpenGL frame buffer. At block 1602, the image is compressed for transmission. At block 1603, the image is transmitted to the VCC clients. More specifically, as described further below, individual portions of an overall image are compressed and transmitted sequentially.

Standard methods for capturing and sending images across a network are generally insufficient for purposes of this embodiment. The most common solutions are MPEG encoding or Apple QuickTime encoding of the video stream, which can be performed with specialized hardware to allow frame rates on the order of 30 frames per second. However, these solutions are limited to NTSC and PAL screen resolutions, which are insufficient for the very high resolutions displays needed for this application (e.g., 1024×1024 true color pixels). Software encoding using these standards is possible, but they are computationally intensive and cannot be performed in real-time on images extracted from the OpenGL frame buffer. Even in the case of single frame transmission, the software implementations of MPEG and QuickTime could take 10–100 times longer than is desired.

Consequently, the present technique employs a run length encoding (RLE) compression routine that can operate on a typical image in less than 70 msec, and provide a compression ratio in the range of 3:1 to 6:1, depending on image content. Even with a 6:1 compression, typical 3D medical images to be transmitted may be about 8 Mb (1024×1024×3×2 for stereo display). A single data stream to a VCC client at 10 frames per second would require 80 Mb/sec. Multiply this bandwidth by the number of clients, and transmission can become extremely difficult. A solution is to use the multicast addressing protocol, which allows a single data stream to leave the graphics server addressed for multiple client receivers. One aspect of the multicast protocol is that the packet size (the basic unit of information transmitted across the network by the protocol) is on the order of 1.5 Kb in size; consequently, the overall image is broken into many packets for transmission. Another aspect of the multicast protocol is that transmission of each piece of information is unreliable—that is, it is impossible to guarantee that a specific packet arrives at a particular client. Because some portion of an image could be lost, and the VCC client must be able to reconstruct a partial image if information is missing, this factor is accounted for in the transmission routines implemented by the graphics server, as described below.

The RLE image encoding must retain all of the image information if it is to be decoded properly. Because information could be lost in transmission, a modified RLE method is used to selectively encode smaller portions of the image that can fit in a single packet. Rather than base the RLE encoding on a specific image size, the compression routine starts compressing data until a specified compressed file size is reached, at which point it restarts and creates a new packet. Finished packets are handed off to the transmission routines, and sent immediately to the VCC clients. Each packet also contains a header specifying where in the whole image this image fragment should be decoded, and which image frame number it belongs to in case fragments of multiple images arrive at a VCC client.

Figure 17:
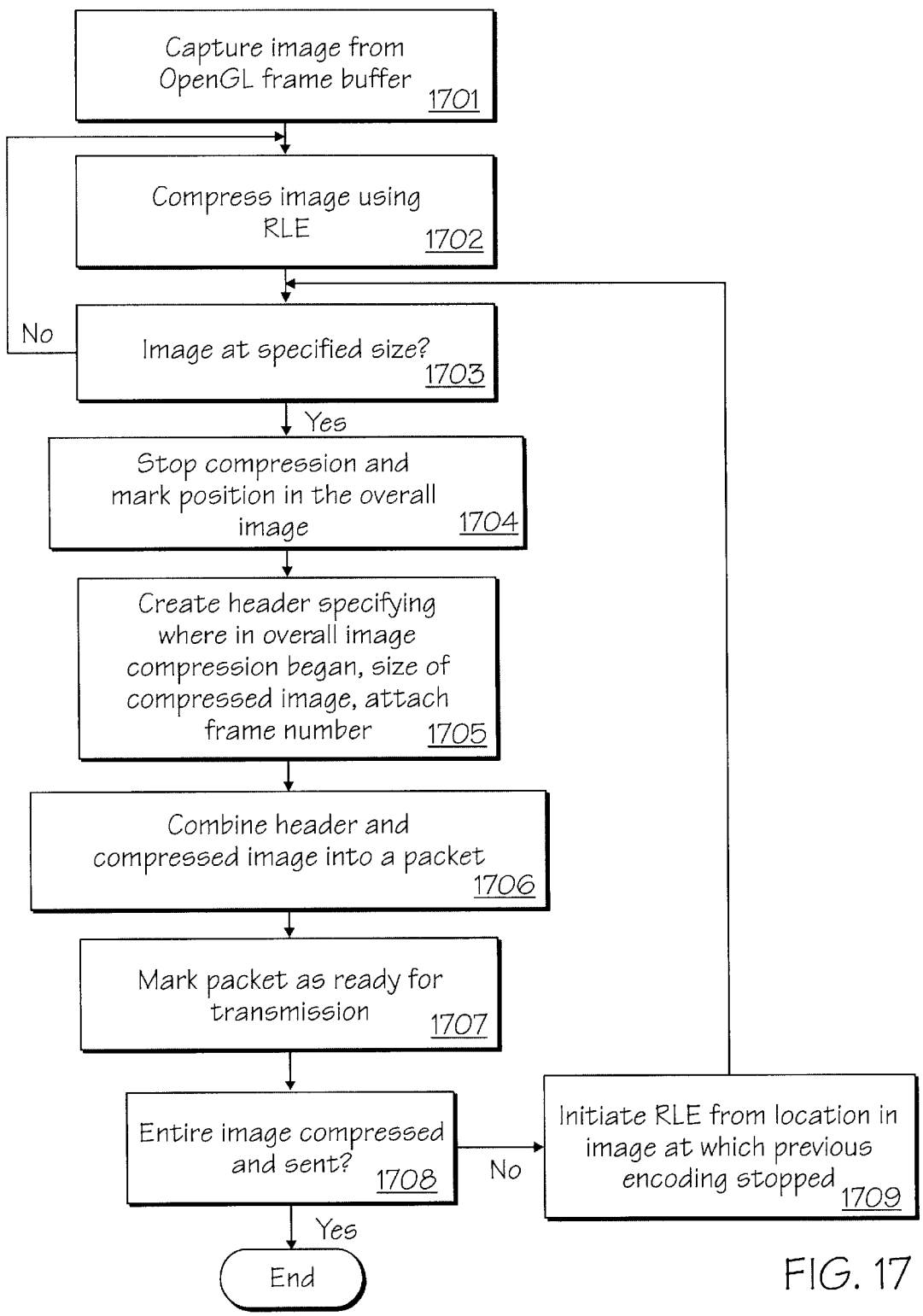
FIG. 17 is a flow diagram illustrating a process executed by the graphics supercomputer for capturing and compressing images.

Thus, the process implemented by the graphics server is described further with reference to FIG. 17. At block 1701, the graphics server captures the image from the OpenGL frame buffer. Next, the server compresses the image using RLE encoding at block 1702, and checks the size of the encoded image at block 1703. When the encoded image reaches the specified size (block 1703), the server marks the position in the image and halts the RLE encoding at block 1704. At block 1705, the server creates a header specifying where in the image the RLE encoding began, exactly how large is the RLE encoded image, and attaches the image frame number generated by the graphics server for this image frame. The server combines the header and RLE encoded image into a packet at block 1706, and marks the packet as ready for transmission at block 1707. If the entire image has been compressed and transmitted (block 1708), then the routine ends; otherwise the RLE compression is reinitiated at block 1709 from the location in the image at which the previous encoding was halted, and routine repeats from block 1703.

At a VCC client, each packet received is decoded and placed in the image at the location specified by the header in the packet. When packets with a larger frame number arrive, the VCC client assumes that all packets have been sent for the current frame and transfers the image to the screen. If packets have been lost, then errors in the image will be seen at the VCC client.

Network equipment that is currently available cannot, in practice, handle the bandwidth required for the applications described above, without substantial loss of data packets. Because a reliable transmission protocol is not available, the data flow coming out of the graphics server is regulated to minimize packet loss, at the expense of frames per second. When transmitting data at a very high data rate, too many packets may be lost, resulting in noticeable image degradation on the client systems. Accordingly, it may be desirable to maintain an average data rate that is lower than the maximum achievable rate, to reduce the number of lost packets. Creating two timers in the graphics server transmission routines, one to regulate inter-packet transmission time and the other to regulate inter-frame transmission time, can be used to accomplish this. These parameters can be modified while the system is operating, so that if network conditions change, the transmission rate can be adjusted accordingly.

Figure 18:
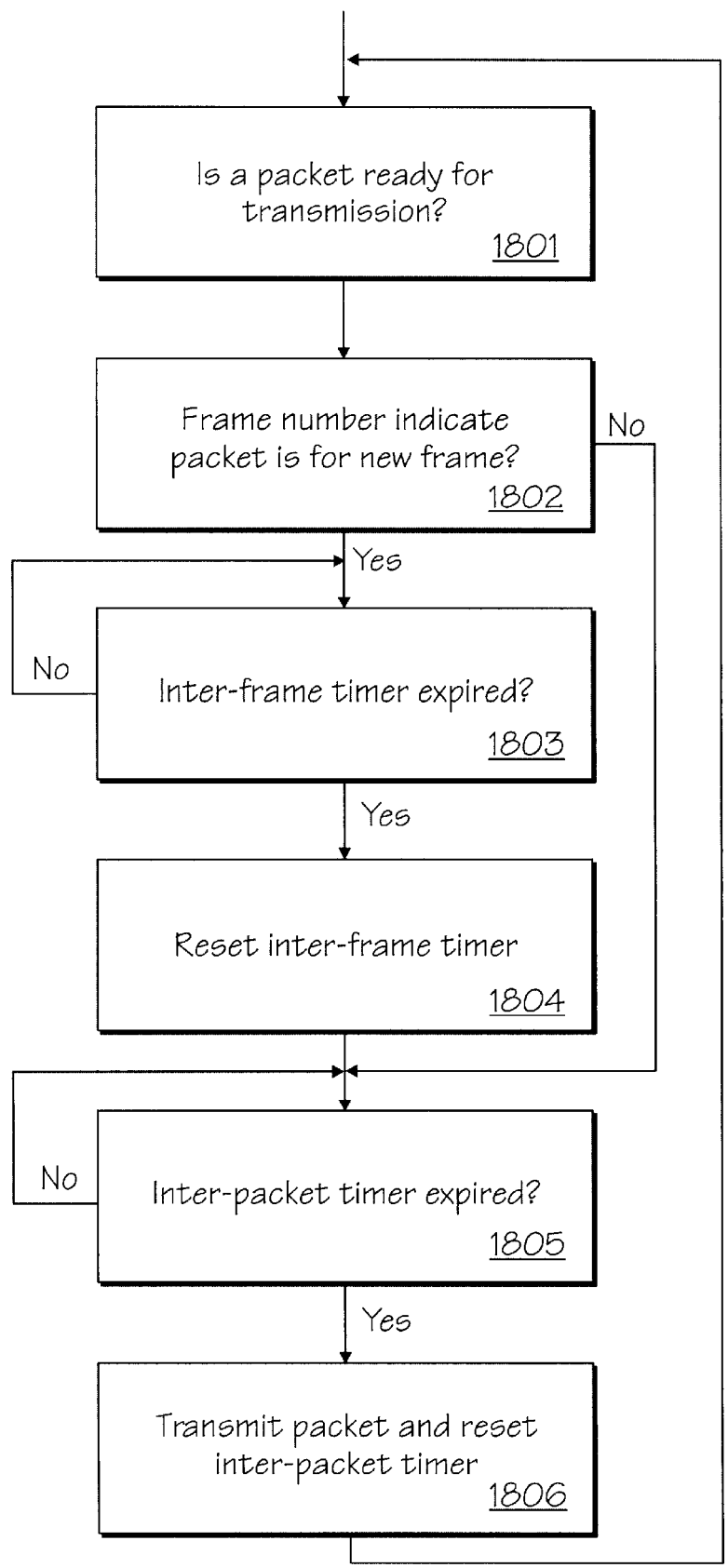
FIG. 18 is a flow diagram showing a process executed by the graphics supercomputer for transmitting packets to VCC clients.

The transmission process, therefore, is described further with reference to FIG. 18. At block 1801, the server determines if a packet is available for transmission. If the frame number of the packet indicates that the packet is for a new frame at block 1802, then it is determined at block 1803 whether the inter-frame timer has expired. If the packet is not for a new frame, the procedure precedes directly to block 1805, described below. If the packet is for a new frame and the inter-frame timer has not expired, the procedure loops at block 1803 until the inter-frame timer has expired. Once the inter-frame timer has expired, the timer is reset at block 1804, and at block 1805, it is determined whether the inter-packet timer has expired. If not, the procedure loops at block 1805 until the inter-packet timer has expired. When the inter-packet timer has expired, the packet is transmitted, and the inter-packet timer is reset at block 1806. The procedure then repeats from block 1801.

Note that the capture, compression, and transmission processes many run in separate threads for greater efficiency. If a single image is being sent, then the sequence of events is serial. However, in the streaming video mode, transmission of a given frame may occur concurrently with compression of the next frame and capture of a subsequent frame. Such concurrent operation allows the frame rate to be limited only by the slowest process of the three and can significantly increase the number of frames sent per second for complex images.

Thus, a method and apparatus have been described for enabling a number of geographically distributed users to collaboratively view and manipulate high-quality, high-resolution, 3D images of anatomical objects based on tomographic data. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative sense rather than a restrictive sense.

What is claimed is:

1. A method of enabling users of a plurality of networked computer systems to collaboratively view and manipulate images of an object, the method comprising:
   causing corresponding images of the object to be displayed on each of a plurality of computer systems at a first resolution;
   receiving, at one of the computer systems, user input specifying a manipulation of the image;
   transmitting information indicative of the user input to each of the other computer systems;
   updating the image displayed on each of the other computer systems substantially simultaneously to depict the manipulation, including displaying the image at a second resolution lower than the first resolution while said manipulation is being depicted; and displaying the image on each of the computer systems at the first resolution when depiction of the manipulation is complete.

2. A method as recited in claim 1, further comprising maintaining a model of the object at the first resolution and a model of the object at the second resolution, wherein said updating comprises switching from using the first model to using the second model to display the image.

3. A method as recited in claim 1, wherein the image displayed by each of the computer systems may be a three-dimensional image.

4. A method as recited in claim 1, wherein said displaying comprises displaying changes of the object over time.

5. A method of enabling a plurality of geographically distributed users to collaboratively view and manipulate images of an object, the method comprising:

maintaining a data structure including data representing the object, the data structure including a plurality of variables shared by each of a plurality of remote processing systems, the data structure further including a plurality of models of the object, each model corresponding to a different image resolution;

multicasting data to each of the remote processing systems based on the data structure to allow the image to be displayed on each of the remote processing systems, including dynamically selecting from the plurality of models; and coordinating transmission of user inputs and values of shared variables applied at each of the client systems to allow the image displayed on each of the client systems to be updated in real-time in response to user inputs applied at each other client system.

6. A method as recited in claim 5, further comprising selecting said models of the object for said multicasting so as to cause the image to be displayed on each of the client systems at a reduced resolution during a user manipulation of the image on one of the client systems.

7. A method as recited in claim 6, wherein at least one of the client systems is configured to display changes of the object over time.

8. A method as recited in claim 5, further comprising, for each of a plurality of consecutive portions of the data representing the object:

compressing the portion until the portion reaches the specified image size; and combining the compressed portion into a packet with information indicating a position of said portion within the image.

9. A method of enabling a plurality of geographically distributed users to collaboratively view and manipulate images of an object in real-time, the method comprising, at a server:

maintaining a data structure including data representing the object, the data structure including a plurality of variables shared by each of a plurality of remote client systems, the data structure further including a plurality of models of the object, each model corresponding to a different image resolution;

sequentially preparing a packet of each of a plurality of consecutive portions of the data representing the object for transmission to the remote client systems, based on the data structure, including selecting said models of the object according to display capabilities of the remote client systems;

multicasting each packet that is ready for transmission to each of the remote client systems to allow each of the client systems to display the image of the object based on the packets; and coordinating transmission of user inputs applied at each of the client systems to allow the image displayed on each of the client systems to be updated in real-time in response to user inputs applied at each of the other client systems.

10. A method as recited in claim 9, wherein said maintaining comprises selecting said models of the object so as to cause the image to be displayed on each of the client systems at a reduced resolution during a user manipulation of the image at one of the client systems.

11. A method as recited in claim 9, wherein said preparing comprises:

compressing the portion until the portion reaches the specified image size;

combining the compressed portion into a packet with information indicating a position of said portion within the image; and marking the packet as ready for transmission.

12. A method as recited in claim 9, wherein said multicasting further comprises regulating a data transmission rate to control the number of packets lost during transmission.

13. A method as recited in claim 9, wherein said coordinating comprises:

receiving values of said shared variables from each of the remote client systems, the values representing user inputs applied at each said remote client system; and using the values to update the data structure.

14. A method of enabling a plurality of geographically distributed users to collaboratively view and manipulate images of an object in real-time, the method comprising, at a server processing system:

maintaining a data structure including data representing the object, the data structure including a plurality of properties of the object and variables shared by each of a plurality of remote client systems, the data structure further including a plurality of models of the object, each model representing an image of the object at a different resolution;

setting a specified image size;

sequentially preparing each of a plurality of consecutive portions of the data representing the object for transmission, based on the data structure, by compressing the portion using run length encoding until the portion reaches the specified image size, combining the compressed portion into a packet with information indicating a position of said portion within the image, and marking the packet as ready for transmission;

sequentially multicasting each said packet that is ready for transmission to each of the client systems to allow each of the client systems to display an image of the object based on the packets; and coordinating transmission of user inputs applied at each of the client systems to allow the image displayed by each of the client systems to be updated in real-time in response to user inputs applied at each other client system, said coordinating including receiving values of said shared variables from each of the remote client systems, the values representing user inputs applied at each said remote client system, and using the values to update the data structure.

15. A method as recited in claim 14, wherein said preparing comprises appropriately accessing said models of the object so as to cause the image to be displayed on each of the client systems at a lowered resolution during a user manipulation of the image one of the client systems.

16. A method as recited in claim 14, wherein said transmitting comprises regulating a data transmission rate to control the number of packets lost during transmission.

17. An apparatus for enabling a plurality of geographically distributed users to collaboratively view and manipulate images of an object, the method comprising:

means for maintaining a data structure including data representing the object, the data structure including a plurality of variables shared by each of a plurality of remote processing systems, the data structure further including a plurality of models of the object, each model corresponding to a different image resolution;

means for multicasting data to each of the remote processing systems based on the data structure to allow the image displayed on each of the remote processing systems, including dynamically selecting from the plurality of models; and means for coordinating transmission of user inputs applied at each of the client systems to allow the image displayed on each of the client systems to be updated in real-time in response to user inputs applied at each other client system.

18. An apparatus as recited in claim 11, further comprising means for selecting said models of the object for said multicasting so as to cause the image to be displayed on each of the client systems at a reduced resolution during a user manipulation of the image on one of the client systems.

19. An apparatus as recited in claim 17, further comprising:

means for compressing each of a plurality of consecutive portions of the data representing the object until each said the portion reaches a specified image size; and means for combining each compressed portion into a packet with information indicating a position of said portion within the image.

20. An apparatus as recited in claim 17, wherein said means for coordinating comprises:

means for receiving values of said shared variables from each of the remote processing systems, the values representing user inputs applied at each said remote client system; and means for using the values to update the data structure.

* * * * *